(12) United States Patent
Cohen et al.

(10) Patent No.: US 9,494,665 B2
(45) Date of Patent: Nov. 15, 2016

(54) MAGNETIC RESONANCE ANALYSIS USING A PLURALITY OF PAIRS OF BIPOLAR GRADIENT PULSES

(75) Inventors: Yoram Cohen, Kfar-Saba (IL); Noam Shemesh, Rehovot (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 795 days.

(21) Appl. No.: 13/806,853

(22) PCT Filed: Jun. 23, 2011

(86) PCT No.: PCT/IL2011/000506
§ 371 (c)(1),
(2), (4) Date: Dec. 26, 2012

(87) PCT Pub. No.: WO2011/161683
PCT Pub. Date: Dec. 29, 2011

(65) Prior Publication Data
US 2013/0106415 A1    May 2, 2013

Related U.S. Application Data

(60) Provisional application No. 61/358,036, filed on Jun. 24, 2010.

(51) Int. Cl.
*G01R 33/44* (2006.01)
*G01N 24/08* (2006.01)
*G01R 33/563* (2006.01)

(52) U.S. Cl.
CPC ............. *G01R 33/44* (2013.01); *G01N 24/081* (2013.01); *G01R 33/56341* (2013.01); *G01R 33/56316* (2013.01)

(58) Field of Classification Search
CPC ............ G01R 33/44; G01R 33/56316; G01R 33/56341; G01N 24/5081
See application file for complete search history.

(56) References Cited

U.S. PATENT DOCUMENTS

| | | | |
|---|---|---|---|
| 4,718,424 A | 1/1988 | Nishimura | |
| 5,225,779 A * | 7/1993 | Parker | G01R 33/563 324/306 |
| 5,278,501 A | 1/1994 | Guilfoyle | |
| 5,565,775 A | 10/1996 | Stallmach et al. | |
| 5,623,207 A * | 4/1997 | Weissenberger ... | G01R 33/5615 324/300 |
| 5,796,252 A | 8/1998 | Kleinberg et al. | |
| 6,310,478 B1 * | 10/2001 | Heid | G01R 33/5613 324/307 |
| 7,253,618 B1 | 8/2007 | Freedman et al. | |
| 8,571,631 B2 * | 10/2013 | Deimling | G01R 33/5613 324/306 |

(Continued)

FOREIGN PATENT DOCUMENTS

| | | |
|---|---|---|
| CN | 1234508 | 11/1999 |
| WO | WO 2011/161683 | 12/2011 |
| WO | WO 2013/021390 | 2/2013 |

OTHER PUBLICATIONS

Communication Pursuant to Article 94(3) EPC Dated Dec. 5, 2013 From the European Patent Office Re. Application No. 11754748.9.

(Continued)

*Primary Examiner* — Dixomara Vargas

(57) ABSTRACT

A magnetic resonance method is disclosed. The method comprises applying to the sample a plurality of pairs of bipolar gradient pulse subsequences, acquiring a magnetic resonance signal from the sample, analyzing the signal, and issuing a report regarding the analysis.

25 Claims, 28 Drawing Sheets

(56) References Cited

U.S. PATENT DOCUMENTS

| | | | |
|---|---|---|---|
| 8,704,515 B2* | 4/2014 | Ozarslan | G01R 33/44 324/307 |
| 2005/0007100 A1 | 1/2005 | Basser et al. | |
| 2007/0238969 A1 | 10/2007 | Song et al. | |
| 2010/0033182 A1 | 2/2010 | Ozarslan et al. | |
| 2011/0095757 A1 | 4/2011 | Nielsen et al. | |
| 2014/0184224 A1 | 7/2014 | Nevo et al. | |

OTHER PUBLICATIONS

Finsterbusch "Extension of the Double-Wave-Vector Diffusion-Weighting Experiment to Multiple Concatenations", Journal of Magnetic Resonance, XP026101436, 198(2): 174-182, Feb. 13, 2009.

Finsterbusch et al. "A Tensor Approach to Double Wave Vector Diffusion-Weighting Experiments on Restricted Diffusion", Journal of Magnetic Resonance, XP025533997, 195(1) 23-32, Nov. 1, 2008.

Notification of Office Action Dated Aug. 20, 2014 From the State Intellectual Property Office of the People's Republic of China Re. Application No. 201180041220.3 and Its Translation Into English.

Search Report Dated Aug. 20, 2014 From the State Intellectual Property Office of the People's Republic of China Re. Application No. 201180041220.3 and Its Translation Into English.

International Search Report and the Written Opinion Dated Dec. 2, 2011 From the International Searching Authority Re. Application No. PCT/IL2011/000506.

Bar-Shir et al. "Crossing Fibers, Diffractions and Nonhomogeneous Magnetic Field: Correction of Artifacts by Bipolar Gradient Pulses", Magnetic Resonance Imaging, 26: 801-808, 2008.

Cory et al. "Applications of Spin Transport as a Probe of Local Geometry", Polym Reprints, 31: 149-150, 1990.

De Panfilis et al. "Positive or Negative Blips? The Effect of Phase Encoding Scheme on Susceptibility-Induced Signal Losses in EPI", NeuroImage, XP004759191, 25(1): 112-121, Mar. 1, 2005. p. 113-116, Fig.1.

Jerschow et al. "Suppression of Convection Artifacts in Stimulation-Echo Diffusion Experiments. Double-Stimulated-Echo Experiments", Journal of Magnetic Resonance, XP004407986, 125(2): 372-375, Apr. 1, 1997. p. 372-374, Fig.1d.

Koch et al. "Compartment Size Estimation With Double Wave Vector Diffusion-Weighted Imaging", Magnetic Resonance in Medicine, 60: 90-101, 2008.

Koch et al. "Compartment Size Estimation With Double Wave Vector Diffusion-Weighted Imaging", Magnetic Resonance in Medicine, XP055009967, 60(1): 90101, Apr. 17, 2008. p. 91-95, Figs.1, 2.

Komlosh et al. "Observation of Microscopic Diffusion Anisotropy in the Spinal Cord Using Double-Pulsed Gradient Spin Echo MRI", Magnetic Resonance in Medicine, 59: 803-809, 2008.

Komlosh et al. "Observation of Microscopic Diffusion Anisotropy in the Spinal Cord Using Double-Pulsed Gradient Spin Echo MRI", Magnetic Resonance in Medicine, XP055009982, 59(4): 803-809, Jan. 1, 2008.

Mitra "Multiple Wave-Vector Extensions of the NMR Pulsed-Field-Gradient Spin-Echo Diffusion Measurement", Physics Review B: Consdensed Matter and Materials Physics, XP007917522, 51(21): 15074-1578, Jun. 1, 1995.

Ozarslan "Compartment Shape Anisotropy (CSA) Revealed by Double Pulsed Field Gradient MR", Journal of Magnetic Resonance, 199: 56-67, 2009.

Ozarslan et al. "MR Diffusion—'Diffraction' Phenomenon in Multi-Pulse-Field-Gradient Experiments", Journal of Magnetic Resonance, XP022301097, 188(2): 285-294, Oct. 1, 2007. p. 286-288, Figs.1, 2.

Özarslan et al. "A General Framework to Quantify the Effect of Restricted Diffusion on the NMR Signal With Applications to Double Pulsed Field Gradient NMR Experiments", The Journal of Chemical Physics, 130: 104702-1-104702-9, 2009.

Özarslan et al. "Microscopic Anisotropy Revealed by NMR Double Pulsed Field Gradient Experiments With Arbitrary Timing Parameters", The Journal of Chemical Physics, 128: 154511-1-154511-11, 2008.

Özarslan et al. "MR Diffusion-'Diffraction' Phenomenon in Multi-Pulse-Field-Gradient Experiments", Journal of Magnetic Resonance, 188: 285-294, 2007.

Schachter et al. "Measurements of Restricted Diffusion Using an Oscillating Gradient Spin-Echo Sequence", Journal of Magnetic Resonance, XP004406771, 147(2): 232-237, Dec. 1, 2000. p. 232-234, Fig.1.

Shemesh et al. "Detection Diffusion-Diffraction Patterns in Size Distribution Phantoms Using Double-Pulsed Field Gradient NMR: Theory and Experiments", The Journal of Chemical Physics, 132: 034703-1-034703-12, 2010.

Shemesh et al. "Measuring Small Compartmental Dimensions With Low-q Angular Double-PGSE NMR: The Effect of Experimental Parameters on Signal Decay", Journal of Magnetic Resonance, 198: 15-23, 2009.

Shemesh et al. "Noninvasive Bipolar Double-Pulsed-Field-Gradient NMR Reveals Signatures for Pore Size and Shape in Polydisperse, Randomly Oriented, Inhomogeneous Porous Media", The Journal of Chemical Physics, XP009153257, 133(4): 44705-1-44705-9, Jul. 28, 2010.

Shemesh et al. "Observation of Restricted Diffusion in the Presence of a Free Diffusion Compartment: Single- and Double-PFG Experiments", Journal of Magnetic Resonance, 200: 214-225, 2009.

Shemesh et al. "The Effect of Experimental Parameters on the Signal Decay in Double-PGSE Experiments: Negative Diffractions and Enhancement of Structural Infoonation", Journal of Magnetic Resonance, 195: 153-161, 2008.

Topgaard et al. "Restricted Self-Diffusion of Water in a Highly Concentrated W/O Emulsion Studied Using Modulated Gradient Spin-Echo NMR", Journal of Magnetic Resonance, XP004408025, 156(2): 195-201, Jun. 1, 2002. p. 195-197, Figs.2, 3.

Weber et al. "Measurement of Apparent Cell Radii Using a Multiple Wave Vector Diffusion Experiment", Magnetic Resonance in Medicine, 61: 1001-1006, 2009.

Weber et al. "Measurement of Apparent Cell Radii Using a Multiple Wave Vector Diffusion Experiment", Magnetic Resonance in Medicine, XP055009985, 61(4): 1001-1006, Feb. 9, 2009.

Zheng et al. "Suppression of Background Gradients in (B0 Gradient-Based) NMR Diffusion Experiments", Concepts in Magenetic Resonance Part A, 30A(5): 261-277, 2007.

Zheng et al. "Suppression of Background Gradients in (B0 Gradient-Based) NMR Diffusion Experiments", Concepts on Magnetic Resonance Part A: Bridging Education and Research, XP055009891, 30A(5): 261-277, Sep. 4, 2007. p. 269-271, Figs.11, 12, p. 273-274, Figs.20, 23.

Basser et al. "Diffusion-Tensor MRI: Theory, Experimental Design and Data Analysis—A Technical Review", NMR in Biomedicine, 15: 456-467, 2002.

Basser et al. "MR Diffusion Tensor Spectroscopy and Imaging", Biophysical Journal, 66: 259-267, Jan. 1994.

Callaghan "NMR Imaging, NMR Diffraction and Applications of Pulsed Gradient Spin Echoes in Porous Media", Magnetic Resonance Imaging, 14(7/8): 701-709, 1996.

Callaghan et al. "Diffraction-Like Effects in NMR Diffusion Studies of Fluids in Porous Solids", Nature, 351: 467-469, Jun. 6, 1991.

Hakansson et al. "Diffraction-Like Effects in a Highly Concentrated W/O Emulsion: A PFG NMR Study", Magnetic Resonance Imaging, 16(5/6): 643-646, 1998.

Horsfield et al. "Applications of Diffusion-Weighted and Diffusion Tensor MRI to White Matter Disease—A Review", NMR in Biomedicine, 15: 570-577, 2002.

Karlicek Jr. et al. "A Modified Pulsed Gradient Technique for Measuring Diffusion in the Presence of Large Background Gradients", Journal of Magnetic Resonance, 37: 75-91, 1980.

Komlosh et al. "Detection of Microscopic Anisotropy in Gray Matter and in a Novel Tissue Phantom Using Double Pulsed Gradient Spin Echo MR", Journal of Magnetic Resonance, 189: 38-45, 2007.

(56) References Cited

OTHER PUBLICATIONS

Kuchel et al. "NMR 'Diffusion-Diffraction' of Water Revealing Alignment of Erythrocytes in a Magnetic Field and Their Dimensions and Membrane Transport Characteristics", Magnetic Resonance in Medicine, MRM, 37(5): 637-643, May 1997.

Mori et al. "Three-Dimensional Tracking of Axonal Projections in the Brain by Magnetic Resonance Imaging", Annals of Neurology, 45(2): 265-269, Feb. 1999.

International Preliminary Report on Patentability Dated Jan. 10, 2013 From the International Bureau of WIPO Re. Application No. PCT/IL2011/000506.

International Search Report and the Written Opinion Dated Nov. 4, 2012 From the International Searching Authority Re. Application No. PCT/IL2012/050307.

Finsterbusch "Numerical Simulations of Short-Mixing-Time Double-Wave-Vector Diffusion-Weighting Experiments With Multiple Concatenations on Whole-Body MR Systems", Journal of Magnetic Resonance, JMR, 207(2): 274-282, Sep. 19, 2010.

Komlosh et al. "Pore Diameter Mapping Using Double Pulsed-Field Gradient MRI and Its Validation Using a Novel Glass Capillary Array Phantom", Journal of Magnetic Resonance, 208(1): 128-135, 2011.

Shemesh et al. "Accurate Noninvasive Measurement of Cell Size and Compartment Shape Anisotropy in Yeast Cells Using Double-Pulsed Field Gradient MR", NMR in Biomedicine, 25(2): 236-246, 2012. Figs.1C, 1D, Fig.6, p. 237-241.

Shemesh et al. "From Single-Pulsed Field Gradient to Double-Pulsed Field Gradient MR: Gleaning New Microstructural Information and Developing New Forms of Contrast in MRI", NMR in Biomedicine, 23(7): 757-780, Aug. 5, 2010. Abstract, p. 759-760, 763, Fig.7A, p. 767.

Shemesh et al. "Microscopic and Compartment Shape Anisotropies in Gray and White Matter Revealed by Angular Bipolar Double-PFG MR", Magnetic Resonance in Medicine, 65(5): 1216-1227, Feb. 28, 2011. Figs.2C, 2D, 5, p. 1218-1220.

Shemesh et al. "Noninvasive Bipolar Double-Pulsed-Field-Gradient NMR Reveals Signatures for Pore Size and Shape in Polydisperse, Randomly Oriented, Inhomogeneous Porous Media", The Journal of Chemical Physics, 133: 044705-1-044705-9, Jul. 22, 2010. Figs.3, 7, p. 044705-5-044705-6.

Shemesh et al. "Overcoming Apparent Susceptibility-Induced Anisotropy (aSIA) by Bipolar Double-Pulsed-Field-Gradient NMR", Journal of Magnetic Resonance, JMR, 212(2): 362-369, Oct. 2011. Figs.3, 6B, 6D, p. 363-364.

Shemesh et al. "Probing Microscoping Architecture of Opaque Heterogeneous Systems Using Double-Pulsed-Field-Gradient NMR", Journal of the American Chemical Society, JACS, 133(15): 6028-6035, Mar. 29, 2011.

Official Action Dated Aug. 1, 2016 From the U.S. Appl. No. 14/237,911.

* cited by examiner

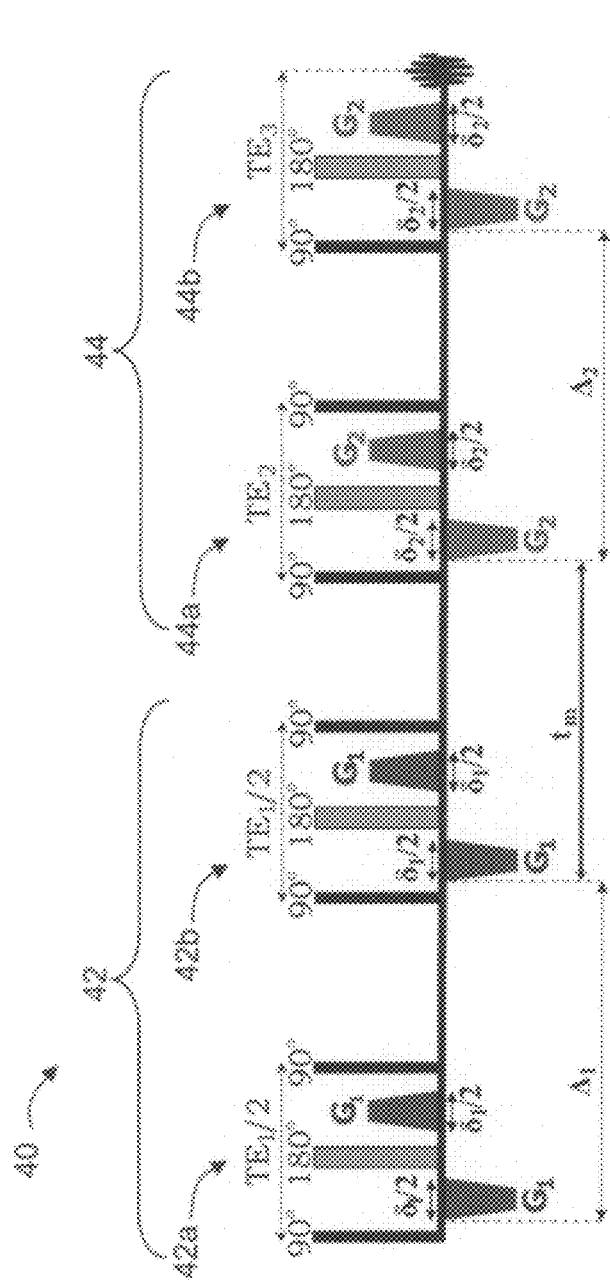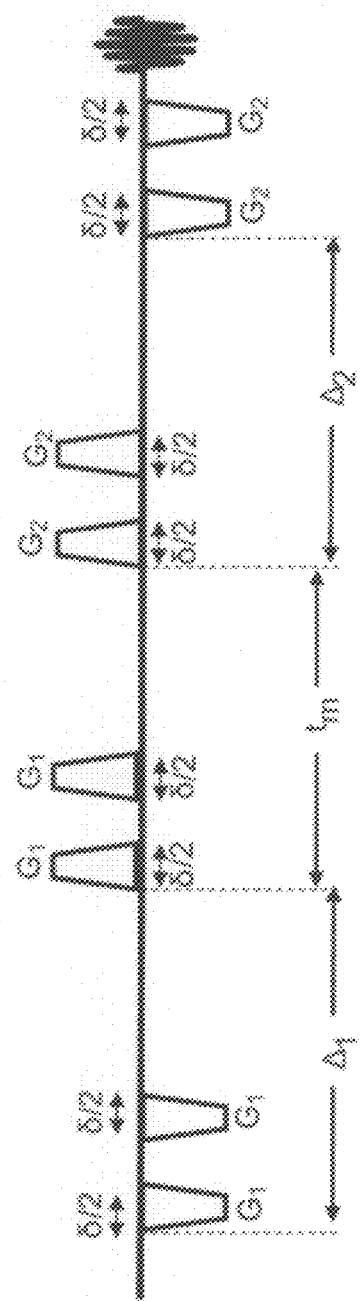
FIG. 4A
FIG. 4B

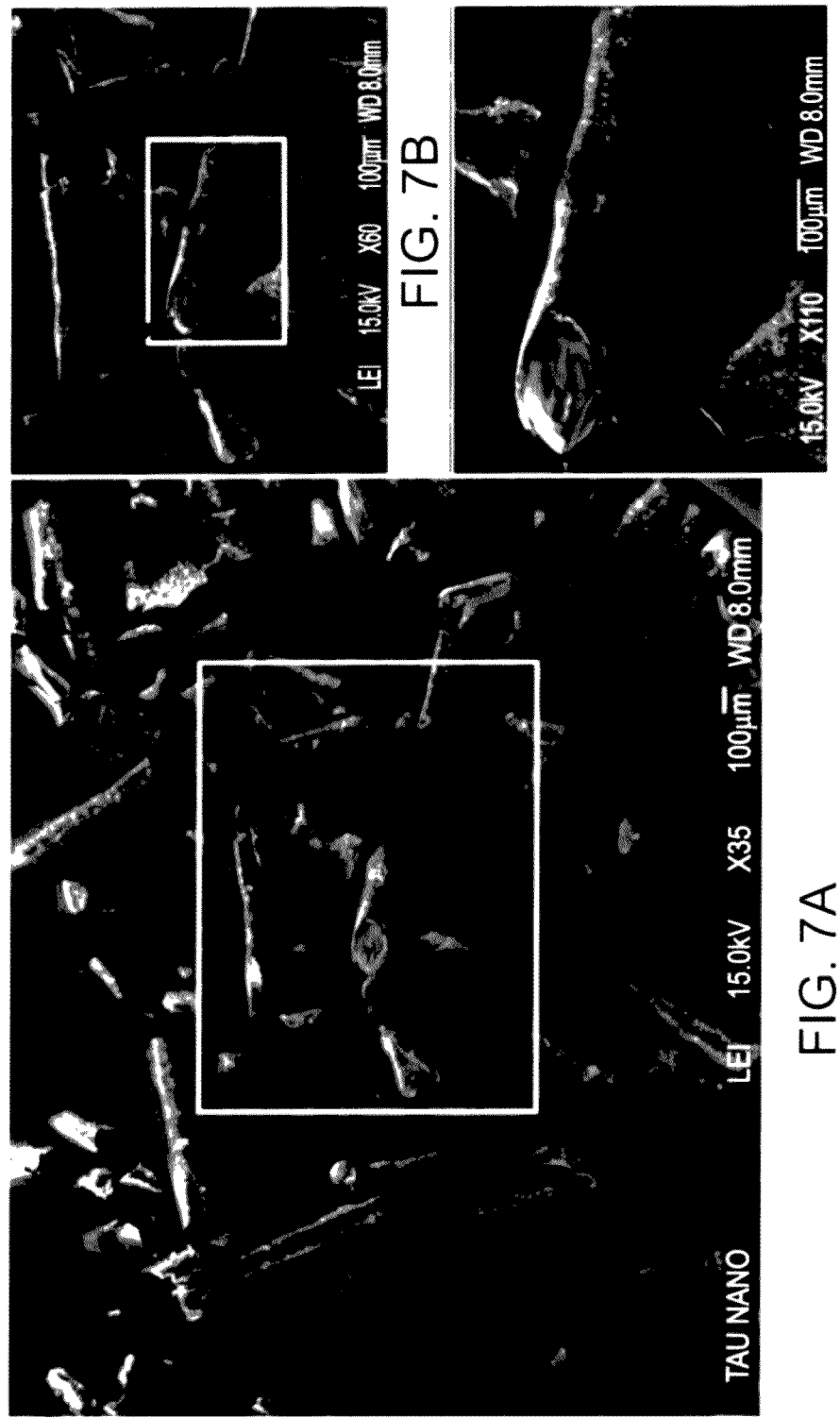

MAGNETIC RESONANCE ANALYSIS USING A PLURALITY OF PAIRS OF BIPOLAR GRADIENT PULSES

RELATED APPLICATION

This application is a National Phase of PCT Patent Application No. PCT/IL2011/000506 having International filing date of Jun. 23, 2011, which claims the benefit of priority under 35 USC §119(e) of U.S. Provisional Patent Application No. 61/358,036 filed on Jun. 24, 2010. The contents of the above applications are all incorporated by reference as if fully set forth herein in their entirety.

FIELD AND BACKGROUND OF THE INVENTION

The present invention, in some embodiments thereof, relates to magnetic resonance analysis and, more particularly, but not exclusively, to magnetic resonance analysis using bipolar gradient pulse subsequences.

Magnetic resonance (MR) analysis is a technique for obtaining the chemical and physical microscopic properties of materials, by utilizing a quantum mechanical phenomenon, named Nuclear Magnetic Resonance (NMR), in which a system of spins, placed in a magnetic field resonantly absorb energy, when applied with a certain frequency.

A nucleus can experience NMR only if its nuclear spin I does not vanish, i.e., the nucleus has at least one unpaired nucleon. Examples of non-zero spin nuclei frequently used in MRI include $^1$H (I=1/2), $^2$H (I=1), $^{23}$Na (I=3/2), etc. When placed in a magnetic field, a nucleus having a spin I is allowed to be in a discrete set of energy levels, the number of which is determined by I, and the separation of which is determined by the gyromagnetic ratio of the nucleus and by the magnetic field. Under the influence of a small perturbation, manifested as a radiofrequency magnetic field, which rotates about the direction of a primary static magnetic field, the nucleus has a time dependent probability to experience a transition from one energy level to another. With a specific frequency of the rotating magnetic field, the transition probability may reach the value of unity. Hence at certain times, a transition is forced on the nucleus, even though the rotating magnetic field may be of small magnitude relative to the primary magnetic field. For an ensemble of spin I nuclei the transitions are realized through a change in the overall magnetization.

Once a change in the magnetization occurs, a system of spins tends to restore its magnetization longitudinal equilibrium value, by the thermodynamic principle of minimal energy. The time constant which control the elapsed time for the system to return to the equilibrium value is called "spin-lattice relaxation time" or "longitudinal relaxation time" and is denoted T1. An additional time constant, T2 (≤T1), called "spin-spin relaxation time" or "transverse relaxation time", controls the elapsed time in which the transverse magnetization diminishes, by the principle of maximal entropy. However, inter-molecule interactions and local variations in the value of the static magnetic field, alter the value of T2, to an actual value denoted T2*.

In MR analysis, pulse sequences are applied to the object to generate NMR signals and obtain information therefrom which is subsequently used to analyze the object. The above mentioned relaxation times and the density distribution of the nuclear spin are properties which vary from one object to the other, and therefore allows the analysis of the object. In diffusion-weighted MR analysis, for example, magnetic field gradients are applied so as to provide motion-related contrast which is sensitive to motion of fluid molecules in selected directions. Diffusion-weighted MR analysis exploits the random motion of the molecules which causes a phase dispersion of the spins with a resultant signal loss. Such analysis can be used for characterizing morphological features of pores that are embedded within porous media, wherein molecules are diffusing within the pores in restricted manner.

A known technique for observing diffusion in porous media employs the so-called pulsed field gradient (PFG) sequence, wherein a pair of magnetic field gradient pulses is applied to encode displacements between the application of these two pulses.

U.S. Pat. No. 7,053,611, for example, discloses a method that includes acquiring a suite of NMR measurements of a fluid sample using a single-polar PFG (s-PFG) sequence for encoding diffusion information, wherein each NMR measurement in the suite is acquired with a different value in a parameter in the pulsed field gradient pulses for producing a different diffusion effect. The suite of NMR measurements is inverted to produce a distribution function that relates diffusion properties of the fluid sample with the longitudinal and/or transverse magnetic relaxation time thereof.

Bipolar PFG sequences have been used in medical imaging applications for measuring diffusion in heterogeneous laboratory samples in which the applied magnetic field is very homogeneous, but produces internal gradients because of the nature of the material of the sample. Additionally, bipolar PFG sequences have been used for measuring diffusion and relaxation of reservoir fluids in the pore spaces of earth formations surrounding a borehole (U.S. Pat. No. 5,796,252).

U.S. Published Application No. 20100033182 teaches a multi-PFG experiment, which involves the application of repeated pairs of diffusion gradients, and in particular a double PFG (d-PFG) sequence which includes two pairs of diffusion gradient pulses. An estimate of the size characteristic of a distribution of restricted compartments of the sample is generated based on the received MR signal.

Additional background art includes G. Zheng and W. S. Price, Concepts Magn. Reson. A 30A, 261 (2007); Bar-Shir and Y. Cohen, Magn. Reson. Imaging 26, 801 (2008); Cory et al., Polymer Preprints 31, 149 (1990); Jerschow and N. Muller, J. Magn. Reson. 125, 372 (1997); E. Özarslan and P. J. Basser, J. Magn. Reson. 188, 285 (2007); E. Özarslan, J. Magn. Reson. 199, 56 (2009); E. Özarslan and P. J. Basser, J. Chem. Phys. 128, 154511 (2008); Özarslan et al., J. Chem. Phys. 130, 104702 (2009); N. Shemesh and Y. Cohen, J. Magn. Reson. 195, 153 (2008); Shemesh et al., J. Magn. Reson. 198, 15 (2009); Shemesh et al., J. Magn Reson. 200, 214 (2009); Shemesh et al., J. Chem. Phys. 132, 034703 (2010); Komlosh et al., Magn. Reson. Med. 59, 803 (2008); M. A. Koch and J. Finsterbusch, Magn. Reson. Med. 60, 90 (2008); and Weber et al., Magn. Reson. Med. 61, 1001 (2009).

SUMMARY OF THE INVENTION

According to an aspect of some embodiments of the present invention there is provided method of magnetic resonance analysis of a sample. The method comprises: applying to the sample a plurality of pairs of bipolar gradient pulse subsequences; acquiring a magnetic resonance signal from the sample; analyzing the signal; and issuing a report regarding the analysis.

According to some embodiments of the invention each pair of bipolar gradient pulse subsequences is characterized by a different gradient direction.

According to some embodiments of the invention two pairs are employed.

According to some embodiments of the invention the method performs a series of experiments, each experiment being characterized by a different angle ψ between the respective gradient directions of the bipolar gradient pulse subsequences.

According to some embodiments of the invention the method comprises analyzing signal profiles as a function of the angle so as to extract shape information and/or size information from the sample.

According to some embodiments of the invention the method comprises generating an estimate of eccentricity distribution of restricted compartments in the sample, thereby providing the shape information.

According to some embodiments of the invention the method comprises analyzing the signal as a function of a magnetic resonance wavenumber so as to generate an estimate of a size distribution of restricted compartments in the sample.

According to an aspect of some embodiments of the present invention there is provided a method of extracting shape information from a porous sample by magnetic resonance analysis. The method comprises: applying to the sample a plurality of pairs of bipolar gradient pulse subsequences, each pair being characterized by a gradient angle; acquiring a magnetic resonance signal as a function of a relative angle among different pairs; analyzing an angular dependence of the signal so as extract at least one of: shape information and size distribution from the sample; and issuing a report regarding the shape information.

According to an aspect of some embodiments of the present invention there is provided a method of characterizing morphological features of porous sample by magnetic resonance analysis, comprising: applying to the sample a plurality of pairs of bipolar gradient pulse subsequences, each pair being characterized by a gradient angle; acquiring a magnetic resonance signal as a function of at least a relative angle among different pairs; and generating an output comprising an intensity profile of the signal as a function of at least the relative angle, thereby characterizing the morphological features of the sample.

According to some embodiments of the invention the method comprises using the magnetic resonance signal from the sample for imaging the sample.

According to an aspect of some embodiments of the present invention there is provided a system for magnetic resonance analysis, comprising; a radiofrequency system configured for generating a plurality of pairs of bipolar gradient pulse subsequences, and acquiring magnetic resonance signals from the sample; and a processing system configured for analyzing the signal, and communicating a report regarding the analysis.

According to some embodiments of the invention each pair of bipolar gradient pulse subsequences is characterized by a different gradient direction.

According to some embodiments of the invention the radiofrequency system is configured for performing a series of experiments, each experiment being characterized by a different angle ψ between the respective gradient directions of the bipolar gradient pulse subsequences, and the processing system is configured for analyzing signal profiles as a function of the angle so as to extract at least one of: shape information and size distribution from the sample.

According to some embodiments of the invention the processing system is configured for generating an estimate of eccentricity distribution of restricted compartments in the sample, to provide the shape information.

According to some embodiments of the invention the processing system is configured for analyzing the signal as a function of a magnetic resonance wavenumber so as to generate an estimate of a size distribution of restricted compartments.

According to some embodiments of the invention the processing system is configured for generating a magnetic resonance image of the sample based on the signal.

According to an aspect of some embodiments of the present invention there is provided a computer software product, comprising a computer-readable medium in which program instructions are stored, which instructions, when read by a computer, cause the computer to instruct a radiofrequency system to generate a plurality of pairs of bipolar gradient pulse subsequences.

According to an aspect of some embodiments of the present invention there is provided a computer software product, comprising a computer-readable medium in which program instructions are stored, which instructions, when read by a computer, cause the computer to receive a recorded magnetic resonance signal in response to a plurality of pairs of bipolar gradient pulse subsequences, to analyze the signal, and to communicate a report regarding the analysis.

According to some embodiments of the invention a mixing time between bipolar gradient pulse subsequences of the pair is selected to allow determination of a shape of pores in the sample.

According to some embodiments of the invention an intensity of the bipolar gradient pulse subsequences is selected to allow identification of at least one of a predetermined compartment shape, a predetermined compartment size and a predetermined compartment organization.

According to some embodiments of the invention the bipolar gradient pulse subsequences are embedded in spin echo sequences.

According to some embodiments of the invention the bipolar gradient pulse subsequences are embedded in stimulated echo sequences.

According to some embodiments of the invention the bipolar gradient pulse subsequences are embedded in gradient echo sequences.

According to some embodiments of the invention the bipolar gradient pulse subsequences are embedded in a combination of sequences selected from the group consisting of spin echo sequences, stimulated echo sequences and gradient echo sequences.

According to some embodiments of the invention the sample is a porous sample.

According to some embodiments of the invention the sample is characterized by NMR line width of at least 10 Hz.

According to some embodiments of the invention the sample is a porous sample characterized by an average pore size of less than 50 microns, with a standard deviation which is at least 3%.

According to some embodiments of the invention the sample is a porous sample characterized by an average pore size of less than 50 microns and the bipolar gradient pulse subsequences are devoid of any gradient pulse having a magnitude which is above than 100 gauss/cm.

According to some embodiments of the invention the sample comprises at least one object selected from the group consisting of a sediment, a rock, a heterogeneous catalyst, a porous material, a porous polymers, an emulsion product, a biological cell, a tissue, a central-nervous-system tissue, quartz sand and a yeast cell.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-D are schematic illustrations of pulse sequences which comprise two pairs of bipolar gradient pulse subsequences (FIGS. 4A and 4C) and the corresponding effective waveforms (FIGS. 4B and 4C).

FIGS. 7A-C are SEM images of a representative porous medium used in experiments performed in accordance with some embodiments of the present invention.

DESCRIPTION OF SPECIFIC EMBODIMENTS OF THE INVENTION

Figure 1:
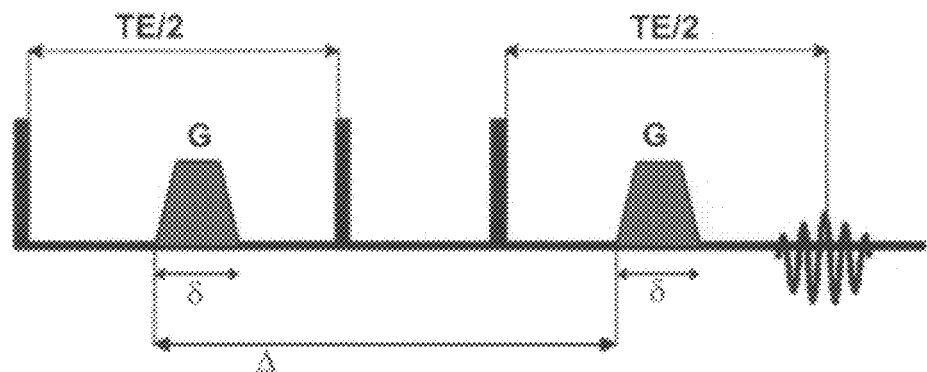
FIG. 1 is a schematic illustration of an s-PFG sequence.

The present invention, in some embodiments thereof, relates to magnetic resonance analysis and, more particularly, but not exclusively, to magnetic resonance analysis using bipolar gradient pulse subsequences.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates an s-PFG sequence (also referred in the literature as a uni-polar PFG sequence). This sequence is composed of one pair of subsequences each having one gradient pulse and one or more radiofrequency pulses. Each gradient pulse is denoted G. The width of each gradient pulse is denoted δ and the time interval between the two gradient pulses is denoted Δ.

The radiofrequency pulses are shown as vertical black bars. In the representative example shown in FIG. 1, the gradient pulses are embedded in the so-called stimulated echo radiofrequency sequence which includes three 90° pulses. Specifically, each gradient pulse is preceded with a 90° radiofrequency pulse, with an additional 90° pulse after the first gradient pulse so that there are two 90° pulses between the gradient pulses. Thus, the first subsequence includes a gradient pulse between two 90° radiofrequency pulses, and can therefore be written symbolically as "90-G-90." The time difference between the first and second 90° pulses of this subsequence is TE/2, where TE denotes the echo time. The second subsequence includes a gradient pulse preceded by a 90° radiofrequency pulse and can therefore be written symbolically as "90-G." The time difference between the 90° pulse of this subsequence and the acquisition time is also TE/2.

The pair of diffusion gradient pulses of the s-PFG sequence sensitizes the MR signal to molecular displacement during the time interval Δ between the two gradients, and the resulting signal decay is a manifestation of the diffusion processes that occur within the excited volume.

Some s-PFG methodologies employ Diffusion Tensor Imaging (DTI) which is conducted at low magnitudes of the MR wavevector q, defined as $q=\gamma \delta G/2\pi$, where γ, δ and $\underline{G}$ are the gyromagnetic ratio, the gradient duration and the gradient vector, respectively.

Throughout this application, vector quantities are denoted using underlined symbols.

The magnitude of the MR wavevector $\underline{q}$ is referred to as the wavenumber and denoted q. Thus, $q=|\underline{q}|$.

In DTI, the diffusion tensor is extracted, and the tensor components yield measures for pore anisotropy. DTI is useful for characterizing coherently placed anisotropic structures in normal and diseased CNS tissues [Basser et al., NMR Biomed. 15, 456 (2002); Mori et al., Ann. Neurol. 45, 265 (1999); and Horsfield et al., NMR Biomed. 15, 570 (2002)].

For higher values of the MR wavenumber, a q-space MR technique is employed. This approach utilizes the diffusion-diffraction patterns that are observed when higher q-values are reached to obtain compartmental dimensions. In q-space MR technique, the pore size can be directly derived from the minimum points of the signal decay, provided that the geometry is known. The diffusion-diffraction patterns are informative since they bear a signature for restricted diffusion. Diffusion-diffraction patterns were experimentally observed in relatively monodisperse specimens such as red blood cells (RBCs) and narrowly distributed emulsions [B. Hakansson et al., Magn. Reson. Imaging 16, 643 (1998), Kuchel et al., Magn. Reson. Med. 37, 637 (1997)].

It was found by the present inventors that conventional s-PFG approaches are inadequate for porous samples in which the pores are placed in incoherent manner or with large variance in their size distribution, particularly when it is desired to extract microstructural information. This is because the diffusion-diffraction minima vanish from the s-PFG signal decay, and the microstructural information is limited and practically lost.

It was further found by the present inventors that s-PFG approaches are inadequate for samples in which the susceptibility differences within the porous medium result in relatively strong susceptibility-induced internal magnetic fields, irrespectively whether the pores are placed coherently or incoherently.

Figure 2A:
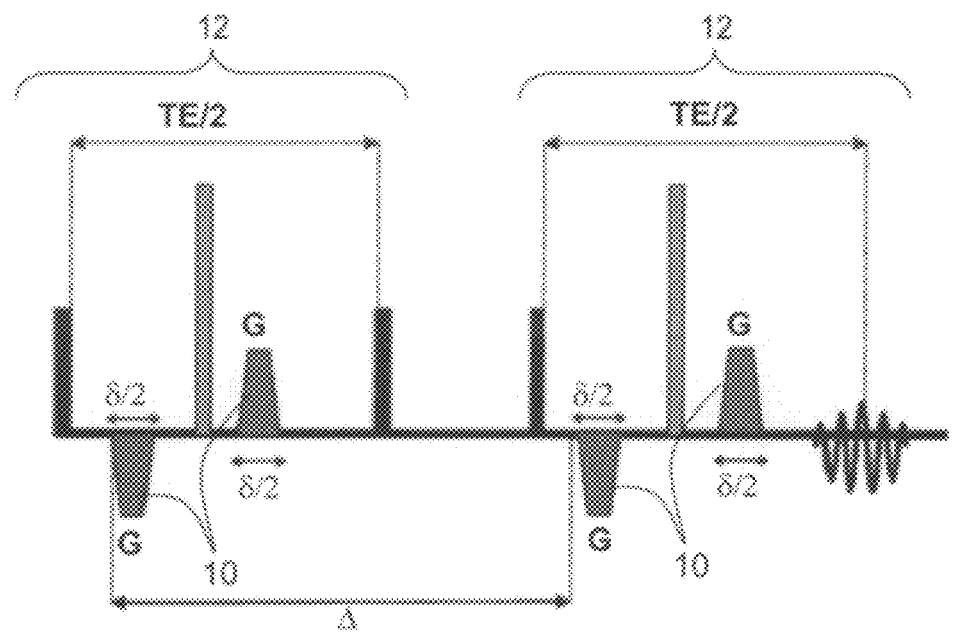
FIGS. 2A-B are schematic illustrations of a single-pair bipolar PFG sequence (FIG. 2A) and the corresponding effective waveform (FIG. 2B).

FIG. 2A illustrates a pulse sequence which is composed of one pair of subsequences each having a pair of bipolar gradient pulses and one or more radiofrequency pulses. This sequence is referred to herein as a single-pair bipolar PFG sequence.

As used herein "pair of bipolar gradient pulses" refers to a pair of gradient pulses applied by activating the gradient coil along some axis at a first amplitude for a first period of time, and then along the same axis for a second period of time and at a second amplitude, wherein the first and second amplitudes are of opposite polarity. For clarity of presentation then term "bipolar pair" will be used as abbreviation for "pair of bipolar gradient pulses."

In some embodiments of the present invention the first and second amplitudes are equal in magnitude (but opposite in their polarity), and in some embodiments of the present invention the first period of time equals the second period of time.

As used herein "a bipolar gradient pulse subsequence" refers to a subsequence which includes at least a bipolar pair. For clarity of presentation then term "bipolar subsequence" will be used as an abbreviation for "bipolar gradient pulse subsequence."

As used herein, "a pair of bipolar subsequences," refers to two successive bipolar subsequences in which the overall time-integral of the gradient pulses constituting the bipolar pair the first bipolar subsequence of the pair equals the overall time-integral of the gradient pulses constituting the bipolar pair the second bipolar subsequence of the pair. Formally, denoting the magnitudes of the gradients of the bipolar pair of the first subsequence by $G_{1a}$ and $G_{1b}$, and the magnitudes of the gradients of the bipolar pair of the first subsequence by $G_{2a}$ and $G_{2b}$, in a pair of bipolar subsequences, the following relation applies:

$$\int_{t1}^{t2} G_{1a} dt + \int_{t3}^{t4} G_{1b} dt = \int_{t5}^{t6} G_{2a} dt + \int_{t7}^{t8} G_{2b} dt$$

where, $t_1, \ldots, t_8$ denote the beginning and end time-points of the respective gradient pulses (e.g., $G_{1a}$ is applied by activating the respective gradient coil at time $t_1$ and deactivating the respective gradient coil at $t_2$; $G_{1b}$ is applied by activating the respective gradient coil at time $t_3$ and deactivating the respective gradient coil at $t_4$, and so on).

A bipolar subsequence may optionally include one or more radiofrequency pulses as known in the art. Representative examples include, without limitation, radiofrequency pulses forming the so called "spin echo" sequence (a 90° pulse followed by a 180° pulse), and radiofrequency pulses forming the aforementioned stimulated echo sequence. In some embodiments of the present invention a bipolar subsequence includes a radiofrequency pulse (e.g., 180° pulse) between the individual gradient pulses of the bipolar pair.

Figure 2B:
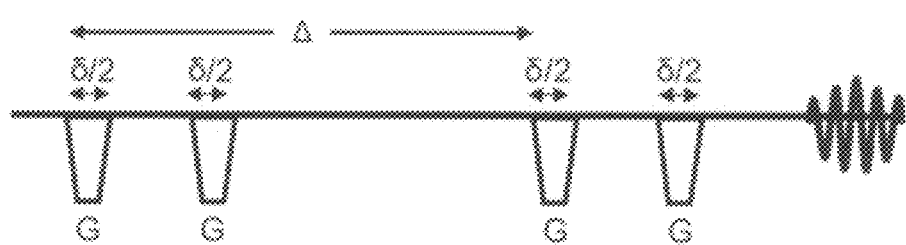

In FIG. 2A, each bipolar pair is designated 10, and each bipolar subsequence is designated 12. In the present example, bipolar subsequence 12 includes bipolar pair 10, a 180° radiofrequency pulse between the individual gradient pulses of bipolar pair 10 and a 90° radiofrequency pulse before the first gradient pulse of bipolar pair 10. The first subsequence also includes a 90° radiofrequency pulse after the second gradient pulse of bipolar pair 10. The resulting waveform associated with the sequence of FIG. 2A is schematically illustrated in FIG. 2B.

The width of each individual gradient pulse of pair 10 is $\delta/2$, namely half the width of a single gradient pulse of the s-PFG pair (cf. FIG. 1). In other words, the total time during which the gradient coils are operative is the same for producing pair 10 as for producing a single gradient pulse in the s-PFG pair. Thus, the difference between the s-PFG sequence and the single-pair bipolar sequence is that in the latter a complex including a bipolar pair and an intermediate 180° pulse is substituted for each gradient pulse of the former.

The single-pair bipolar PFG reduces the contribution from the scalar product of the applied and static gradient vectors, and recovers diffusion-diffraction patterns in inhomogeneous magnetic field.

The present inventor found that in many cases the single-pair bipolar PFG sequence is inadequate, particularly when it is desired to extract information regarding the shape and orientation of pores in a porous medium. This is because there are cases in which such a sequence induces an MR signal decay which is not sufficiently informative to allow distinction between features originating from the shape of the pores and features originating from their orientation. Consider, for example, a scenario in which an isotropic MR signal decay is induced by a single-pair bipolar PFG sequence applied to some porous medium. In this scenario, it is difficult to determine whether the isotropic signal is indicative of spherical pores or elongated pores which are randomly oriented over some region. In such a signal, it is difficult even to identify presence of restricted diffusion.

Figure 3A:
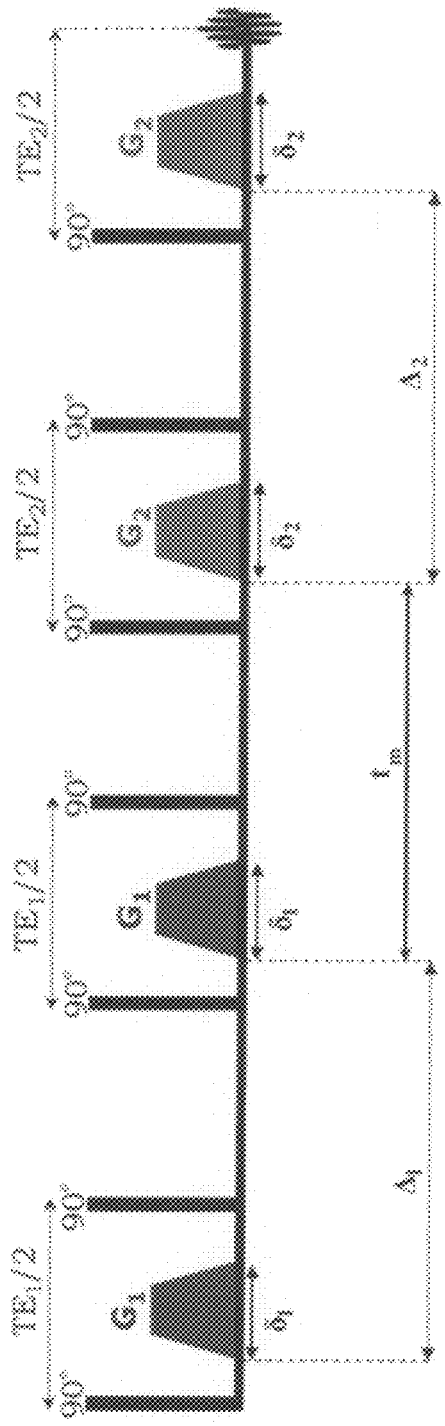
FIGS. 3A-B are schematic illustrations of d-PFG sequences.
Figure 3B:
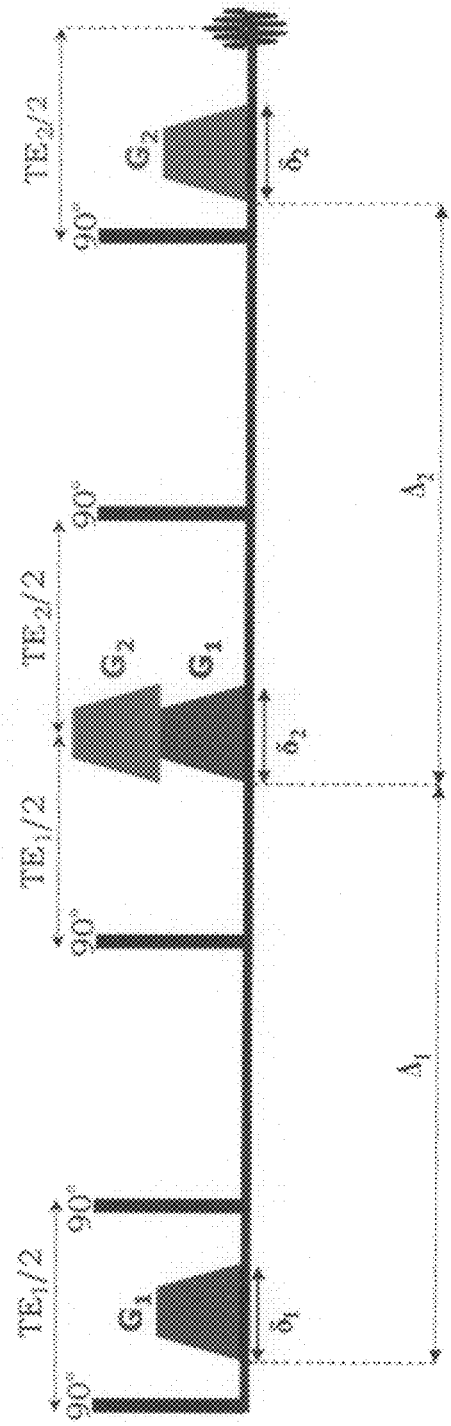

FIGS. 3A-B illustrate d-PFG sequences. Each d-PFG sequence comprises two s-PFG sequences, namely two pairs of gradient pulses and several radiofrequency pulses. The gradient pulses of the first gradient pair are denoted $G_1$, and the gradient pulses of the second gradient pair are denoted $G_2$. $G_1$ and $G_2$ are typically at an angle $\psi$ (not shown in FIGS. 3A-B) with respect to each other. The widths of $G_1$ and $G_2$ are denoted $\delta_1$ and $\delta_2$, respectively; the time interval between the first $G_1$ and the second $G_1$ is denoted $\Delta_1$; the time interval between the first $G_2$ and the second $G_2$ is denoted $\Delta_2$; and the time interval between the second $G_1$ and the first $G_2$, which is also referred to as the mixing time, is denoted $t_m$. FIG. 3A illustrates a d-PFG sequence with $t_m > 0$ and FIG. 3B illustrates a d-PFG sequence with $t_m = 0$.

As in FIGS. 1 and 2A above, the radiofrequency pulses are shown in FIGS. 3A-B as vertical black bars. The sequence in FIG. 3A includes four sequential subsequences, using the above symbolic notation, these subsequences can be written as "90-$G_1$-90", "90-$G_1$-90", "90-$G_2$-90" and "90-$G_2$". For the first and second subsequences, the time interval between the two 90° pulses of the respective subsequence, are denoted $TE_1/2$ for the first and second subsequence and $TE_1/2$ for the third subsequence, and the time interval between the 90° pulse of the fourth subsequence and the acquisition time is $TE_2/2$.

The sequence in FIG. 3B includes three sequential subsequences, "90-$G_1$-90", "90-$G_1G_2$-90" and "90-$G_2$", where "$G_1G_2$" is to be understood that $G_1$ is applied simultaneously with $G_2$. In first and last subsequences, the time intervals between the two 90° pulses are denotes $TE_1/2$ and $TE_2/2$, respectively. In the second subsequence, the time interval between the first 90° pulse and the simultaneous gradient pulses is $TE_1/2$, and the time interval between the simultaneous gradient pulses and between the second first 90° pulse is $TE_2/2$.

The MR signal induced by the d-PFG sequence typically becomes negative at about half the wave number necessary to observe the non-monotonicity in s-PFG. This effect is referred to as zero-crossing and is analogous to the diffusion-diffraction minima in s-PFG. The zero-crossing is advantageous since it allows reducing the gradient strength, and allows determining an average pore size more robustly even when the sample contains pores with a broad distribution of sizes or pores that are locally anisotropic and randomly distributed [Özarslan and Basser 2007, Özarslan 2009, and Shemesh et al. 2010, supra].

Another advantage of the zero-crossings of the MR signal induced by the d-PFG sequence is that it can be used for obtaining microstructural information. This is because the q-value of zero-crossing is indicative, at least qualitatively, of the average size of the pores, and the rate of return to the ambient noise level is indicative of the width of the distribution.

An additional advantage of d-PFG is that the angular parameter $\psi$ can be used for extracting additional information. For example, local pore shape can be derived from the dependence of the signal intensity, E, on $\psi$ at different q-values, particularly at long mixing times, since the E($\psi$) curves are indicative of compartment shape anisotropy.

It was found by the inventors that in the presence of inhomogeneous magnetic fields many of the above advantages of the d-PFG sequences are absent. The present inventors discovered an effect in which randomly oriented pores generate an anisotropic signal decay. The effect is contrary to the common belief that any anisotropy in signal decay is indicative of coherent orientation [to this end see, e.g., Mitra, Phys. Rev. B, 1995, 51, 15074; and Özarslan 2009, Özarslan et al. 2008, Özarslan et al. 2009, supra]. Thus, the discovered effect may lead to erroneous conclusion that the orientations of the pores have some preferred direction. It is assumed by the present inventors that such anisotropy is originated from strong susceptibility-induced internal magnetic fields within the porous medium. The discovered effect is referred to herein as apparent-Susceptibility Induced Anisotropy (aSIA).

The present inventor found that the aSIA effect is generated in response to application of conventional pulse sequences such as conventional s-PFG and d-PFG sequences. The present inventor found that although the aSIA effect can be suppressed using a single-pair bipolar PFG sequence, this solution is inadequate since, as stated, it provides information which is insufficient for distinguishing between shape features and orientation features.

While reducing the present invention to practice it has been unexpectedly uncovered that it is advantageous to employ a pulse sequence which includes a plurality of pairs of bipolar gradient pulse subsequences. Two representative examples of such a pulse sequence are schematically illustrated in FIGS. 4A-D.

While the embodiments below are described with a particular emphasis to two pairs of bipolar subsequences, it is to be understood that more detailed reference to two pairs is not to be interpreted as limiting the scope of the invention in any way, since the pulse sequence of the present embodiments can include two or more (e.g., three or four or five) pairs of bipolar subsequences.

FIG. 4A illustrates a sequence 40, which comprises two pairs 42, 44 of bipolar subsequences. The bipolar subsequences of first pair 42 are designated 42a and 42b, and the bipolar subsequences of second pair 44 are designated 44a and 44b. The gradient pulses of pairs 42 and 44 are denoted $G_1$, and $G_2$, respectively. Since subsequences 42a, 42b, 44a and 44b are bipolar subsequences each of these subsequences comprises a bipolar pair, as further described in detail above.

In various exemplary embodiments of the invention each of subsequences 42a, 42b, 44a and 44b further comprises one or more radiofrequency pulses. The present inventors contemplate many types of radiofrequency pulses, and it is not intended to limit the scope of the present invention to any specific radiofrequency sequence. Representative example of radiofrequency pulse sequences in which the subsequences of the present embodiments can be embedded include, without limitation, spin echo sequences, stimulated echo sequences, gradient echo sequences and any combination thereof. Optionally and preferably, there is a 180° pulse between the individual gradient pulses of each bipolar pair. In some embodiments, each bipolar pair is preceded by a 90° pulse. In this embodiment, there are two 90° pulses between successive bipolar pairs.

FIG. 4B shows the resulting effective waveform corresponding to the pulse sequence shown in FIG. 4A. The first two $G_1$ gradients in FIG. 4B, correspond to the decomposition of the first $G_1$ gradient pulse of FIG. 3A into two gradients each having a duration of $\delta/2$. These two gradients are dephasing, while the two next gradients (corresponding to the decomposition of the second $G_1$ gradient pulse in FIG. 3A) are both applied in a refocusing sense. The third and fourth gradients (corresponding to the decomposition of the first $G_2$ gradient pulse in FIG. 3A) are again dephasing, while the last two gradients (corresponding to the decomposition of the second $G_2$ gradient pulse in FIG. 3A) are applied in a refocusing sense to the two preceding gradients.

In the representative illustrations of FIGS. 4A-4D, all gradient pulses of pair 42 have equal widths ($\delta_1/2$) and equal amplitudes in absolute value ($G_1$), and all gradient pulses of pair 44 have equal widths ($\delta_2/2$) and equal amplitudes in absolute value ($G_2$), but this need not necessarily be the case since the gradient pulses need not to be of equals width or of equal amplitude, provided they satisfy the aforementioned relation regarding a pair of bipolar subsequences, Specifically, for each pair of bipolar subsequences in sequence 40, the overall time-integral of the gradient pulses constituting the bipolar pair the first subsequence of the pair equals the overall time-integral of the gradient pulses constituting the bipolar pair the second subsequence of the pair.

In some embodiments of the present invention sequence 40 comprises at least one bipolar pair in which both gradient pulses have equals widths and equal amplitudes (but opposite in polarity).

In some embodiments of the present invention sequence 40 comprises at least one pair of bipolar subsequences in which all gradient pulses have equals widths and equal amplitudes (in absolute value).

Although the gradient pulses in FIGS. 4A-D are shown as having a trapezoidal profile, this need not necessarily be the case. The presence embodiments contemplate gradient pulses of any shape, e.g., rectangular, Gaussian, and the like.

The time interval between the first and second bipolar pairs of the ith pair of subsequences (measured, e.g., between the first gradient pulses of the bipolar pairs) is denoted $\Delta_i$. The mixing time between pair i of subsequences and pair i+1 of subsequences is denoted $t_{m,i}$. For clarity of presentation, the symbol $t_m$ will be used below for the embodiments in which sequence 40 includes only two pairs. Shown in FIG. 4A are $\delta_1$, $\delta_2$, $\Delta_1$, $\Delta_2$ and $t_m$.

Figure 4C:
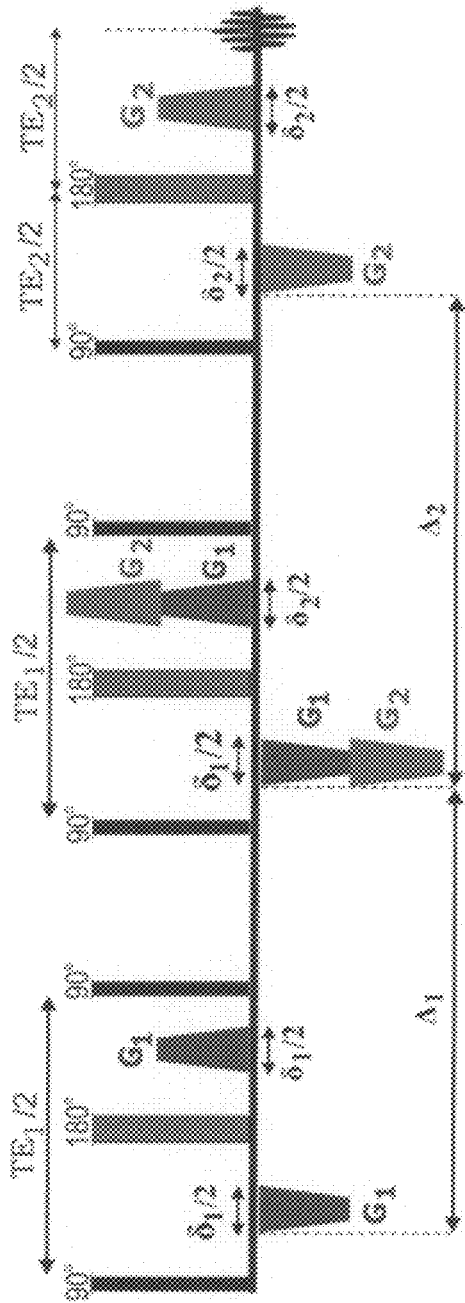
Figure 4D:
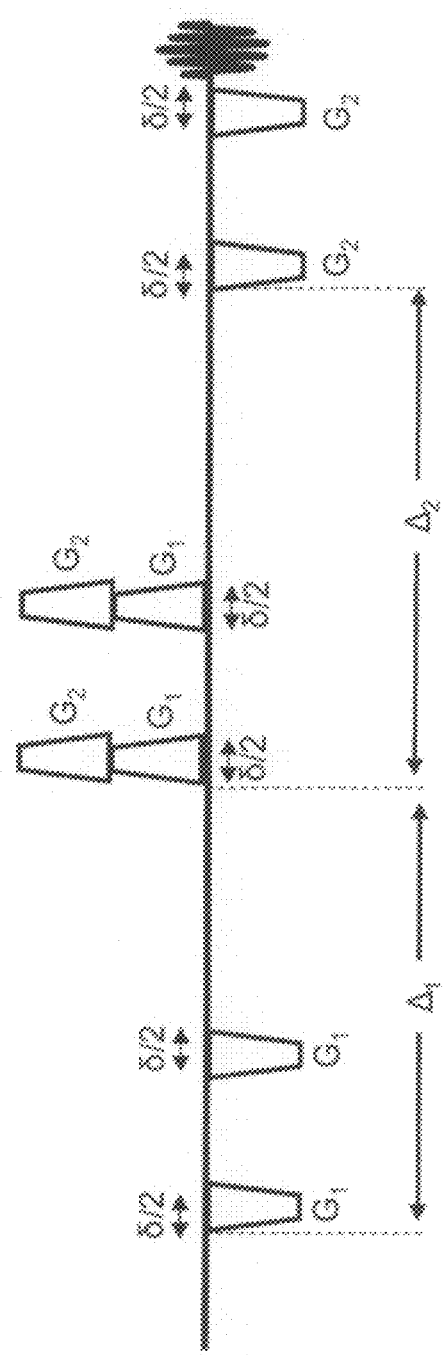

For any two pairs of bipolar subsequences, the respective mixing time can be finite (i.e., non-zero) or zero, as desired. FIG. 4C schematically illustrates an embodiment in which sequence 40 includes two pairs with $t_m$=0, and FIG. 4D shows the corresponding waveform.

In some embodiments of the invention the mixing time between bipolar subsequences is selected to allow determination of the shape of the pores in sample under analysis, and in some embodiments of the invention the mixing time is selected to allow detecting the presence, or estimating the level of, microscopic anisotropy or isotropy.

When it is desired to analyzed the sample in terms of microscopic anisotropy or isotropy, the mixing time is preferably short, typically much shorter than (e.g., less than a tenth) of the ratio $d^2/D$, where d is the characteristic restricting length scale of the sample, and D is the diffusion coefficient. The characteristic restricting length scale is measured in units of length, e.g., microns, and the diffusion coefficient is measured in unites of area per unit time (e.g., $\mu m^2/ms$). For example, the mixing time can be set to zero.

When it is desired to analyzed the sample in terms of the shape of the pores, the mixing time is preferably long, typically on the order of the ratio $d^2/D$ or longer. Preferably, for determining the presence or estimating the level of compartment shape anisotropy or isotropy, the mixing time is above 10 ms for small specimens where the typical diameters are smaller, for example in nerve tissues, or on the order of 50 ms for some length scales in rocks.

In various exemplary embodiments of the invention each of at least a few of the pairs of bipolar sequences, more preferably each pair of bipolar sequences, is characterized by a different gradient direction. For example, when there are two pairs of bipolar sequences, the (four) gradient pulses of the second pair ($G_2$ in FIGS. 4A-D) are at an angle $\psi$ with respect to the gradient pulses of the first pair ($G_1$ in FIGS. 4A-D).

The angle between the gradients of different pair of bipolar sequences is optionally and preferably utilized for extracting shape information from the sample. In these embodiments, relatively long mixing times (e.g., on the order of ratio $d^2/D$ or longer) are preferably, but not necessarily, employed. Shape information can be extracted by analyzing optionally plotting signal profiles as a function of $\psi$, e.g., $E(\psi)$, wherein the dependence of E on $\psi$ is used for determining the shape of the pores in the sample. For example, a generally flat dependence of $E(\psi)$ on $\psi$ can indicate that the pores have low eccentricity (e.g., spherical) and a non-monotonic dependence of $E(\psi)$ on $\psi$ (e.g., a modulated curve of E as a function of $\psi$) can indicate that the pores are non-spherical (e.g., elongated).

In some embodiments, the angle between the gradients of different pair of bipolar sequences is utilized for extracting size information (e.g., characteristic length scale and/or size distribution) from the sample. In these embodiments, relatively short mixing times, typically less than $d^2/D$ (e.g., a tenth or less) are preferably employed. Size information can be extracted by analyzing optionally plotting signal profiles as a function of ψ, e.g., E(ψ), wherein the dependence of E on ψ is used for determining the size of the pores in the sample. Such analysis can include fitting the ψ dependence to a theoretical function, or use of a library of curves or the like. The ψ dependence at short mixing times can optionally and preferably be utilized also for extracting shape information.

Thus, the present embodiments contemplate extraction of various morphological features, including shape and size information, wherein long mixing times are preferred for extracting shape information, and short mixing times are preferred for extracting shape and size information.

The intensity of the gradient pulses, which effects the value of the wavenumber, is preferably selected in accordance with the sample under analysis. Generally, the modulation intensity increases with the wavenumber. Thus, for example, for samples with relatively narrow size-distributions, for example, with standard deviation of less than 10%, the q-value is preferably selected to allow observing relatively robust modulations (e.g., 5% modulation or more) in the signal. On the other hand, for wide size-distributions, for example, with standard deviation of more than 10%, the signal is optionally and preferably analyzed as a function of the wavenumber, e.g., E(q), wherein the dependence of E on q is used for estimating the characteristic length scale or size distribution of the pores in the sample.

Before providing a further detailed description of some embodiments of the present invention, attention will be given to the advantages and potential applications offered by the inventive pulse sequence.

The sequence of the present embodiments allows at least partial suppression of internal magnetic fields that are prominent in many chemical, biomedical and geological applications.

The sequence of the present embodiments is useful for both coherently organized compartments and randomly oriented anisotropic pores in the presence of inhomogeneous fields. As demonstrated in the Examples section that follows, the zero-crossings in the MR signal induced by the sequence of the present embodiments persists in controlled heterogeneous porous media even in the presence of severe internal magnetic fields and random orientation of locally anisotropic pores. Thus, the sequence of the present embodiments overcomes the problems associated with the discovered aSIA effect.

The zero-crossings sensitivity of the MR signal induced by the sequence of the present embodiments is sufficient to estimate a mean value of a restricted compartment size distribution of porous media with accuracy of several microns. The sensitivity is also sufficient for analyzing porous media having broad size distribution. As representative example, the sequence of the present embodiments induces an MR signal with an identifiable zero-crossing for size distribution characterized by a width (e.g., standard deviation) which is at least 3% or at least 5% or at least 10% or at least 20% or at least 30% or at least 40% or at least 50% of the mean value.

The present embodiments successfully provide a technique which allows observing compartment shape anisotropy at long mixing times and inferring local compartment shape even when pores are randomly oriented.

Thus, unlike conventional magnetic resonance techniques, the technique of the present embodiments is capable of characterizing porous media that have all degrees of complexity found in nature, including, without limitation, random orientation of locally anisotropic pores, size polydispersity and internal magnetic fields.

The sequence of the present embodiments allows extracting morphological information from the sample using gradients of relatively low magnitudes. Typically, the sequence of the present embodiments employs gradients at magnitudes of less than 100 gauss/cm or less than 80 gauss/cm or less than 60 gauss/cm or less than 40 gauss/cm or less than 20 gauss/cm. In some embodiments of the present invention the gradients' magnitude is above 2 gauss/cm or above 3 gauss/cm or above 4 gauss/cm or above 5 gauss/cm. It was found by the present inventors that the above ranges of gradient magnitudes are suitable for extracting morphological information from any sample, including, without limitation, samples exhibiting non-Gaussian diffusion having a compartment size distribution characterized by a mean value of at least 1 µm. Thus in various exemplary embodiments of the invention sequence 40 is devoid of gradient pulses whose magnitude is outside the above ranges.

The present embodiments can be utilized in many applications, particularly in those applications in which it is desired to extract, in a non-destructive manner, morphological information relating to porous structures. The sequence of the present embodiments is particularly useful for analyzing a porous medium with heterogenic attributes. Representative examples of samples and objects which can be analyzed using the pulse sequence of the present embodiments include, without limitation, porous materials, biological cells, tissues, central-nervous-system (CNS) microstructures, particularly grey matter in the CNS, porous polymers, liquid crystals, heterogeneous catalysts, emulsion systems, porous rocks and other sediments.

Figure 5:
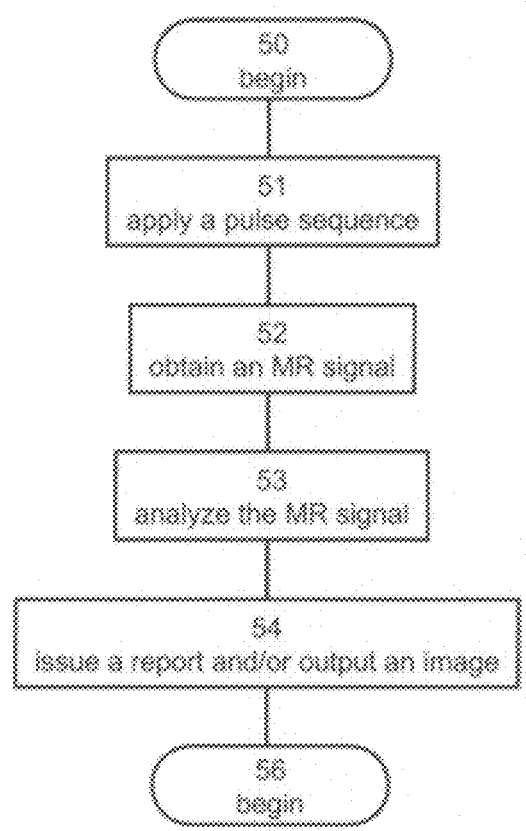
FIG. 5 is a flowchart diagram describing a method suitable for magnetic resonance analysis of a sample according to some embodiments of the present invention.

Reference is now made to FIG. 5 which is a flowchart diagram describing a method suitable for magnetic resonance analysis of a sample, according to some embodiments of the present invention.

One or more of the operations described below can be performed by a data processor. The operations can be embodied on a tangible medium such as a computer for performing the method steps. They can be embodied on a computer readable medium, comprising computer readable instructions for carrying out the operations. They can also be embodied in electronic device having digital computer capabilities arranged to run the computer program on the tangible medium or execute the instruction on a computer readable medium.

Computer programs implementing the method of this invention can commonly be distributed to users on a distribution medium such as, but not limited to, a floppy disk, CD-ROM, portable hard drive or a flash drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

One or more of the operations described below can be performed using a magnetic resonance system. A representative example of a system suitable for the present embodiments is described below.

The method begins at 50 and optionally and preferably continues to 51 at which a pulse sequence is applied to a sample. The sample can be of any type, e.g., the aforementioned types of sample.

Preferably, the sample is a porous sample. The porous sample can be characterized by an average pore size of from about 1 micron, or about 2 microns or about 3 microns or about 4 microns or about 5 microns, to several hundreds of microns. In some embodiments of the present invention the porous sample can be characterized by an average pore size of less than 50 microns or less than 40 microns or less than 30 microns or less than 20 microns or less 10 microns, with a standard deviation which is at least 3% or at least 5% or at least 10% or at least 20% or at least 30% or at least 40% or at least 50%. In some embodiments, the sample is characterized by NMR line width of at least 10 Hz or at least 20 Hz or at least 30 Hz or at least 50 Hz or at least 100 Hz or at least 300 Hz or at least 600 Hz or at least 900 Hz or at least 1200 Hz.

In some embodiments of the present invention the sequence is applied with gradients magnitudes of from about 5 gauss/cm to about 20 gauss/cm to a sample characterized by a mean restricted compartment size of from about 5 µm to about 20 µm.

The pulse sequence preferably comprises a plurality of pairs of bipolar gradient pulse subsequences, as further detailed hereinabove. For example, in some embodiments sequence 40 is used. The method proceeds to 52 at which an MR signal is obtained. The MR signal can be received directly from the MR system that applies the pulse sequence or it can be a previously recorded signal, in which case the method receives the signal from the medium on which the signal is recorded. For example, the method can receive the MR signal from a computer readable medium on which the MR signal has been recorded previously.

The method continues to 53 at which the MR signal is analyzed and optionally and preferably to 54 at which a report regarding the analysis is issued. The report can be displayed on a display device, printed, or recorded on a computer readable medium from which it can be retrieved for further use.

The analysis can include any procedure known in the art for analyzing an MR signal induced by a PFG sequence.

It will be appreciated that the wavenumber q and the angle between gradients $\omega$ span a two-dimensional space over which a two-variable function can be defined and analyzed. In various exemplary embodiments of the invention the signal intensity E is defined as a two-variable function, $E(q, \omega)$. The two-variable function can be analyzed in accordance with some embodiments of the present invention by keeping q fixed and varying $\omega$, or by keeping $\omega$ fixed and varying q, or by varying both q and $\omega$. Analysis at fixed value of $\omega$ can be performed at $\omega=0$, although other angles are not excluded from the scope of the present invention. When the analysis is at a fixed value of q, the value of q is preferably selected in accordance with the typical length scales in the sample under investigation. Any of these scenarios can be utilized for extracting from the MR signal morphological information describing the structure of the sample under investigation.

For example, in some embodiments of the present invention the analysis includes estimation of characteristic length scale or restricted compartment distribution of the sample. A representative example includes the mean value of the restricted compartment size distribution can be estimated. In some embodiments of the present invention the mean value is estimated by analyzing the dependence of the MR signal on the wavevector or wavenumber. An estimate can be provided based on determination of a wavenumber value associated with a local minimum value or zero-crossing (namely change of sign) of the MR signal. In some embodiments of the present invention the mean value is associated with a radius or diameter of the restricted compartments.

In some embodiments of the present invention the mean value is estimated by analyzing the dependence of the MR signal on the angle $\psi$, in particular at relatively short mixing times.

Also contemplated is analysis in which the restricted compartment orientation distribution is estimated. This can be achieved by identifying isotropic or anisotropic features in the MR signal, typically as a function of the wavevector or wavenumber. Signal which is predominantly isotropic indicate a generally isotropic orientation distribution, whereas signal which is predominantly anisotropic indicate that the restricted compartments are aligned in a generally coherent manner.

Representative examples of size and orientation distribution assessments are provided in the Examples section that follows.

In some embodiments of the present invention, the analysis includes extracting shape information from the signal. This is preferably performed by analyzing signal profiles as a function of the relative angle $\psi$ between gradients, preferably, but not necessarily, at relatively long mixing times. In these embodiments, the MR signal features data corresponding to several different angles, and the dependence of the profile is determined and assessed. In some embodiments of the present invention the dependence of the signal on the angle is used for generating an estimate of eccentricity distribution of restricted compartments in the sample, thereby extracting shape information from the MR signal. Such estimate can be obtained by fitting the $\psi$ dependence to a theoretical function, or use of a library of curves or the like.

Data corresponding to different angles can be obtained by repeating the application of the pulse sequence several times, each time with a different value of $\psi$. Thus, the method can optionally loop back from 52 to 51 one or more times. This is equivalent to a sequence with many pairs of bipolar subsequences with several acquisition period thereamongst.

Representative examples of shape information extraction are provided in the Examples section that follows.

In some embodiments of the present invention the MR signal is used for generating an MR image of the sample. Such image can be generated using any MRI technique known in the art (to this end see, e.g., Stark and Bradley (Eds.), 1998, "Magnetic Resonance Imaging," 4th ed., C. V. Mosby). The MR image can be transmitted to a computer readable medium or a display device or a printing system.

Figure 6:
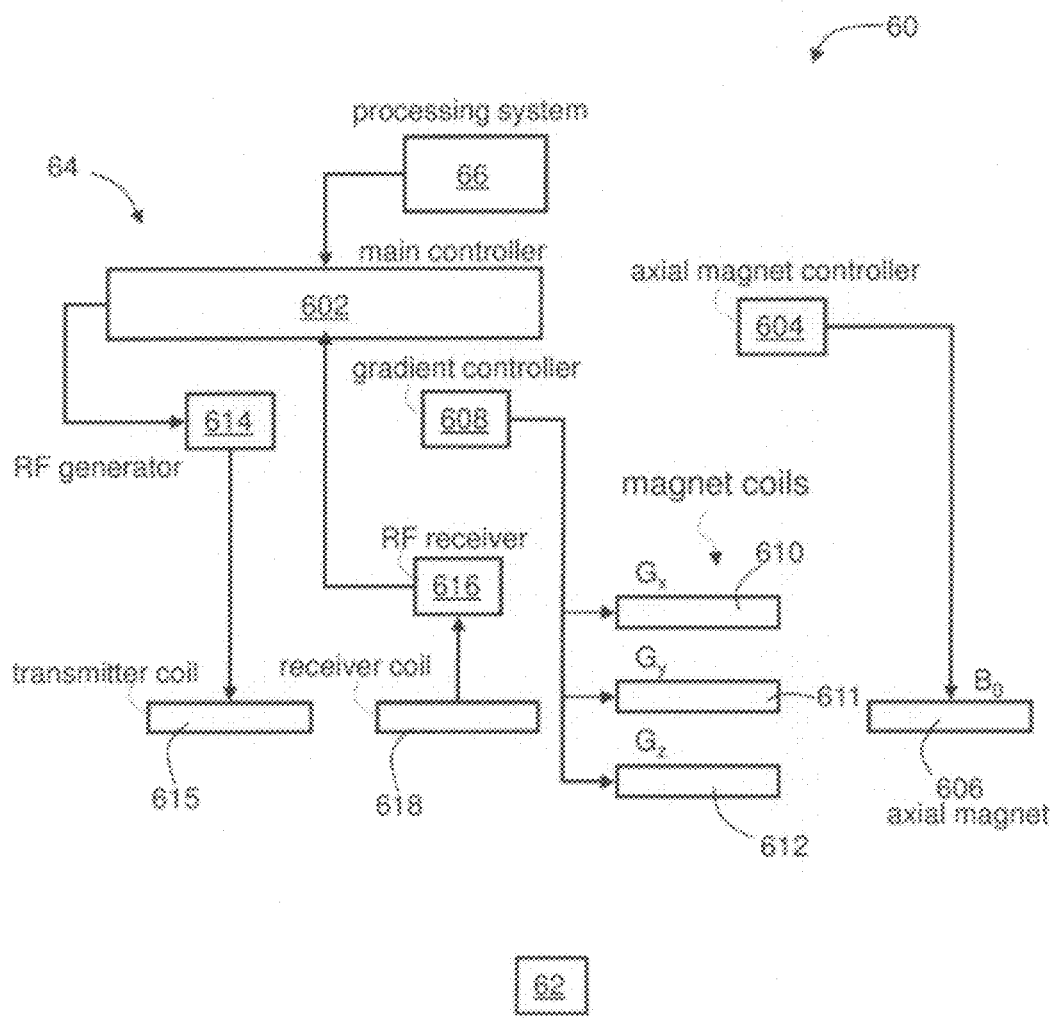
FIG. 6 is a schematic illustration of a system for magnetic resonance analysis of a sample, according to some embodiments of the present invention.

Reference is now made to FIG. 6 which is a schematic illustration of a system 60 for magnetic resonance analysis of a sample 62, according to some embodiments of the present invention.

System 60 comprises a radiofrequency system 64 configured for generating a pulse sequence, applying the pulses of the sequence to sample 62, and acquiring magnetic resonance signals from sample 62. The pulse sequence preferably comprises a plurality of pairs of bipolar subsequences, as further detailed hereinabove. System 60 optionally and preferably comprises a processing system 66 configured for analyzing the signal, and communicating a report regarding the analysis.

System 64 can be of any type known in the art. In the representative and non-limiting example illustrated in FIG. 6, system 64 comprises a main controller 602 which is configured to apply magnetic fields to sample 62. An axial magnet controller 604 is in communication with an axial magnet 606 that is generally configured to produce a substantially constant magnetic field $B_0$. A gradient controller 608 is configured to apply a constant or time-varying gradient magnetic field in a selected direction or in a set of directions using magnet coils 610-612 to produce respective magnetic field gradients $G_x$, $G_y$, $G_z$, or combinations thereof. A radiofrequency generator 614 is configured to deliver one or more radiofrequency pulses to sample 62 using a transmitter coil 615. A radiofrequency receiver 616 is in communication with a receiver coil 618 and is configured to detect or measure net magnetization of spins. Slice selection gradients can be applied with the same hardware used to apply the diffusion gradients.

Gradient controller 608 can be configured to produce the gradient pulses of the present embodiments along one or more axes. Gradient controller 608 can also be configured to apply gradient pulses of different magnitudes (which effect different q-values), and associated MR signals can be detected by the receiver 616.

Main controller 602 communicates with data processing system 66, and is configured for receiving control signals from system 66 and/or transmitting acquisition data (digital or analog) to system 66 for performing the analysis. System 66 can be, for example, a personal computer, a workstation, a personal digital assistant, or a networked computer. System 66 generally includes a hard disk, a removable storage medium such as a floppy disk or CD-ROM, and other memory such as random access memory (RAM). Computer-executable instructions for data acquisition or control can be provided to system 66 as described above.

Preferably, system 66 carries on at least some of the operations described above. For example, system 66 can be loaded with a computer software product which causes the system 66 to instruct radiofrequency system 64 to generate a plurality of pairs of bipolar gradient pulse subsequences. System 66 can also be loaded with a computer software product which causes system 66 to receive from system 64 an MR signal in response to a plurality of pairs of bipolar gradient pulse subsequences, to analyze signal, and to communicate a report regarding analysis, e.g., to a display device.

It is expected that during the life of a patent maturing from this application many relevant magnetic resonance analysis systems will be developed and the scope of the term magnetic resonance analysis system is intended to include all such new technologies a priori.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Materials and Methods

Specimen Preparation

Hollow microcapillaries with well defined inner diameter (ID) (PolyMicro Technologies, Phoenix Ariz., USA) were immersed in distilled water for several days prior to each experiment. The water-filled microcapillaries were manually cut to very small pieces (<0.5 cm) and then crushed by mechanical force to "dust"-like small particles. In some cases, the microcapillaries were not crushed but only cut into very small pieces that enabled random orientation within the NMR tube. The resulting porous medium was re-immersed in water for several days, to refill. The porous crush was then poured to an 8 or in some cases 10 mm NMR tube containing Fluorinert (Sigma-Aldrich, Rehovot, Israel). The Fluorinert served, owing to density and polarity differences, to keep any extra-tubular water in the top part of the NMR tube, which was located outside the RF coils.

The polydisperse specimen was prepared in the same way, only instead of using monodisperse microcapillaries, a mix of microcapillaries of varying sizes was used. Specifically, we used the specimen denoted SD003 in a recently published study, which encompasses microcapillaries with five different inner diameters. The mean±stdv inner diameter of this specimen is 14.9±4.6 µm.

SEM Experiments

Characterization of the morphology and orientation of the porous media was performed using High Resolution Scanning Electron Microscope (HRSEM, JEOL 6700F operated at 15 KeV) equipped with a secondary-electron detector.

NMR Experiments

The NMR tube containing the porous medium was placed in a Bruker 8.4 T NMR spectrometer equipped with a Micro5 probe capable of producing nominal pulsed gradients up to 1900 mT/m in each direction. The temperature was kept constant throughout the experiments. The length of the hard π/2 pulses in all specimens was 15±1 µs.

The following pulse sequences were used: (i) s-PFG, (ii) single-pair bipolar PFG sequence (denoted below bp-s-PFG), (iii) d-PFG, and (iv) a pulse sequence which included two pairs of bipolar gradient pulse subsequences (denoted below bp-d-PFG), in accordance with some embodiments of the present invention.

Randomly Oriented Pores with ID=29±1 µm

The s-PFG and bp-s-PFG experiments were conducted using the sequences shown in FIGS. 1 and 2A respectively, with the following parameters: $\Delta/\delta=250/3$ ms, 32 q-values were collected with $G_{max}$ of 600 mT/m, resulting in a maximum q-value of 766 cm$^{-1}$. The number of scans was set to 32.

The d-PFG and bp-d-PFG experiments were performed using the sequences shown in FIGS. 3B and 4C respectively, and with the following parameters: $\Delta_1=\Delta_2=250$ ms, $\delta_1=\delta_2=\delta_3=3$ ms and $t_m=0$ ms. A total of 32 points were collected with $G_{max}=300$ mT/m resulting in a $q_{max}$ of 383 cm$^{-1}$.

Randomly Oriented Pores with ID=19±1 µm

The s-PFG and bp-s-PFG were conducted with the sequences shown in FIGS. 1 and 2A, respectively, $\Delta/\delta=200/3$ ms, and with $G_{max}$ of 800 mT/m, resulting in a maximum q-value of 1022 cm$^{-1}$.

The d-PFG and bp-d-PFG experiments were performed using the sequences shown in FIGS. 3B and 4C respectively, and with the following parameters: $\Delta_1=\Delta_2=200$ ms, $\delta_1=\delta_2=\delta_3=3$ ms and $t_m=0$ ms. A total of 24 q-values were collected with $G_{max}=400$ mT/m resulting in a $q_{max}$ of 510.5 cm$^{-1}$.

Randomly Oriented Polydisperse Pores

The s-PFG and bp-s-PFG were conducted with the sequences shown in FIGS. 1 and 2A, respectively with $\Delta/\delta=150/3$ ms, and 32 q-values were collected with $G_{max}$ of 1600 mT/m, resulting in a maximum q-value of 2043 cm$^{-1}$.

The bp-d-PFG experiments were performed using the sequences shown in FIGS. 3B and 4C respectively, and with the following parameters: $\Delta_1=\Delta_2=150$ ms, $\delta_1=\delta_2=\delta_3=3$ ms and $t_m=0$ ms. A total of 32 q-values was collected, with $G_{max}=800$ mT/m resulting in a $q_{max}$ of 1021.5 cm$^{-1}$.

Randomly Oriented Pores with ID=10±1 µm

To show compartment shape anisotropy, the angular bp-d-PFG experiments were performed as described previously, using the sequences shown in FIGS. 2A and 3A with the following parameters: $\Delta_1=\Delta_2=150$ ms, $\delta_1=\delta_2=3$ ms and $t_m=18$ ms. Briefly, $\underline{G}_1$ was fixed in the x-direction, and the orientation of $\underline{G}_2$ was varied in 25 equal steps along 360° in the X-Y plane (perpendicular to the direction of $B_0$). In these angular d-PFG experiments $|\underline{G}_1|=|\underline{G}_2|$.

Results

FIGS. 7A-C are SEM images of a representative porous medium used in experiments performed in accordance with some embodiments of the present invention. FIG. 7A shows the random orientation of the pores; FIG. 7B, which is a magnification of the white box in FIG. 7A, shows the local cylindrical geometry of the pores; FIG. 7C is a magnification of the white box in FIG. 7B. The inner diameter of the cylinders (marked by arrowheads) measured from these images was found to be about 28 µm.

The SEM images of the porous medium phantom demonstrate that the pores are randomly oriented (FIG. 7A). The NMR line width in these specimens was about 0.5 kHz indicating on the inhomogeneity of the sample, a manifestation of the relatively large susceptibility effects arising from the random orientation of the cylindrical pores.

Zero-Crossings in Monodisperse, Locally Anisotropic Pores

To determine the microstructural information that can be extracted, s-PFG and d-PFG experiments were performed on a controlled monodisperse porous medium with randomly oriented locally cylindrical pores. To overcome the large susceptibility-induced internal fields, bp-s-PFG and bp-d-PFG sequences were implemented (the sequences are shown in FIG. 2A and FIG. 4 respectively). Introducing bi-polar gradients and carefully timing the sequences partially suppresses the effects of deleterious background gradients and internal magnetic fields and even to restore diffusion-diffraction patterns when pores were coherently placed.

The results are shown in FIGS. 8A-E, where theoretical predictions are shown as solid lines, and experimental data are shown as symbols. Full symbols represent positive-valued signal and empty symbols represent negative-valued signals.

Figure 8A:
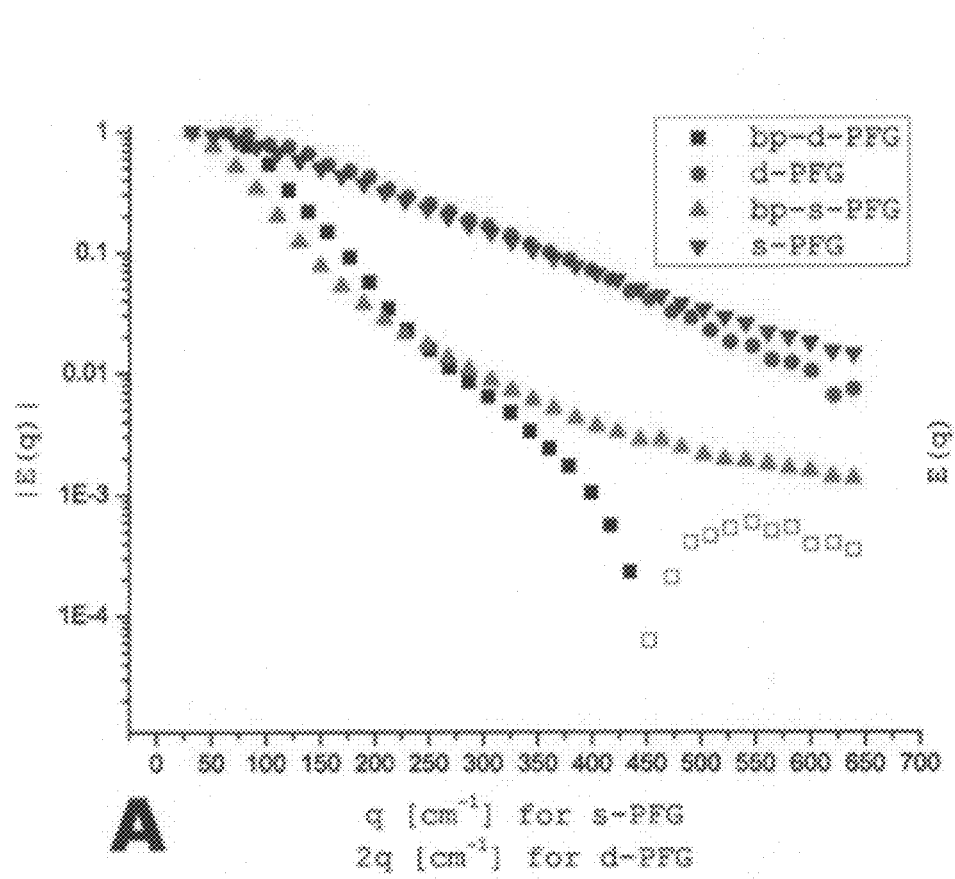
FIGS. 8A-E show signal profiles as a function of the wavenumber as obtained in experiments performed according to some embodiments of the present invention on a sample with locally anisotropic pores having a size distribution of 29±1 μm.

FIG. 8A shows results of the experiments performed a controlled porous medium with nominal ID=29±1 µm shown in FIG. 7. The s-PFG data are plotted against q, while d-PFG data are plotted against 2q for easy comparison. The experiment performed using the s-PFG sequence shown in FIG. 1 yielded a featureless decay, which was clearly affected by the large susceptibility artifact. The signal in the bp-s-PFG experiments (sequence shown in FIG. 2A) attenuated somewhat more than in the s-PFG experiments; however, diffusion-diffraction troughs were not observed (FIG. 8A). When d-PFG experiments were performed using the sequence shown in FIG. 3B, the signal decay was again featureless and no microstructural information could be obtained directly from these E(2q) plots.

Figure 8B:
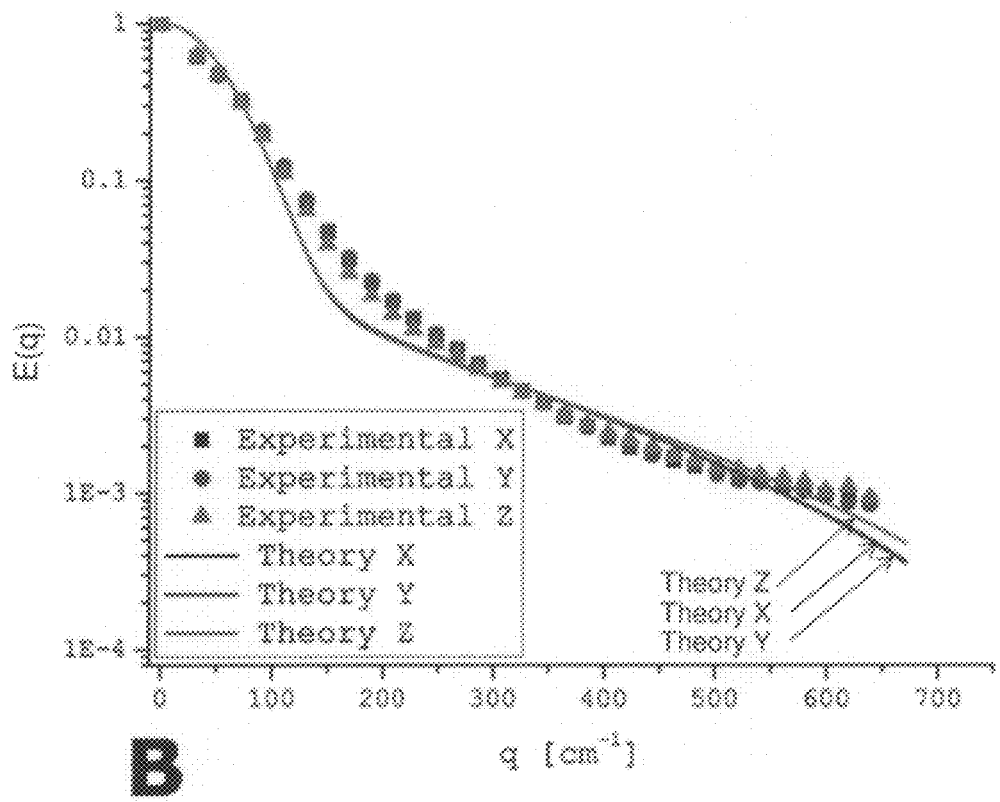
Figure 8C:
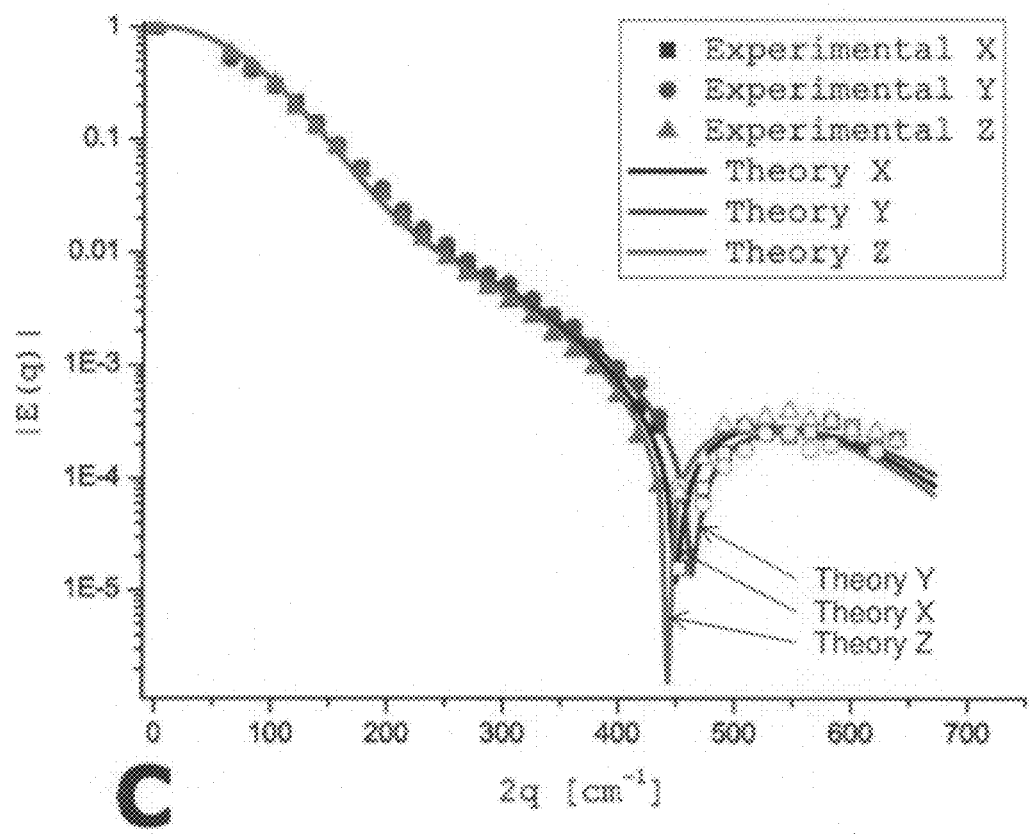

By contrast, the signal decay induced by the bp-d-PFG sequence of the present embodiments (FIG. 4C), is dramatically different: it clearly reveals the zero-crossings (manifested as diffusion-diffraction troughs when |E(2q)| is plotted) arising from restricted diffusion within the constituent pores (FIG. 8A). FIG. 8E shows the actual zero-crossing, occurring at 2q=452 cm$^{-1}$, and shows that indeed the signal turns to negative values at q-values greater than the zero-crossing. This is manifested as an inverted peak in the actual NMR signal decay. The signal decay was fitted to the theory, and the size that was obtained was 28.00±0.03 µm, in excellent agreement with the nominal ID of the pores (29±1 µm).

To show that the pores are indeed randomly oriented both bp-s-PFG and bp-d-PFG experiments were performed in x-, y- and z-directions. FIGS. 8B and 8C show the absolute value of the signal decay induced by the bp-s-PFG sequence and the inventive bp-d-PFG sequence, respectively. The bp-d-PFG of the present embodiments demonstrates a zero-crossing (manifested as a diffusion-diffraction trough in the absolute valued plot) in all directions at similar q-values, while in bp-s-PFG, the diffusion-diffraction minima are absent for all directions. The isotropic signal decay implies that there is no preference for a certain orientation of the pores within the NMR tube, and therefore the pores in the specimen are indeed completely randomly oriented.

Figure 8D:
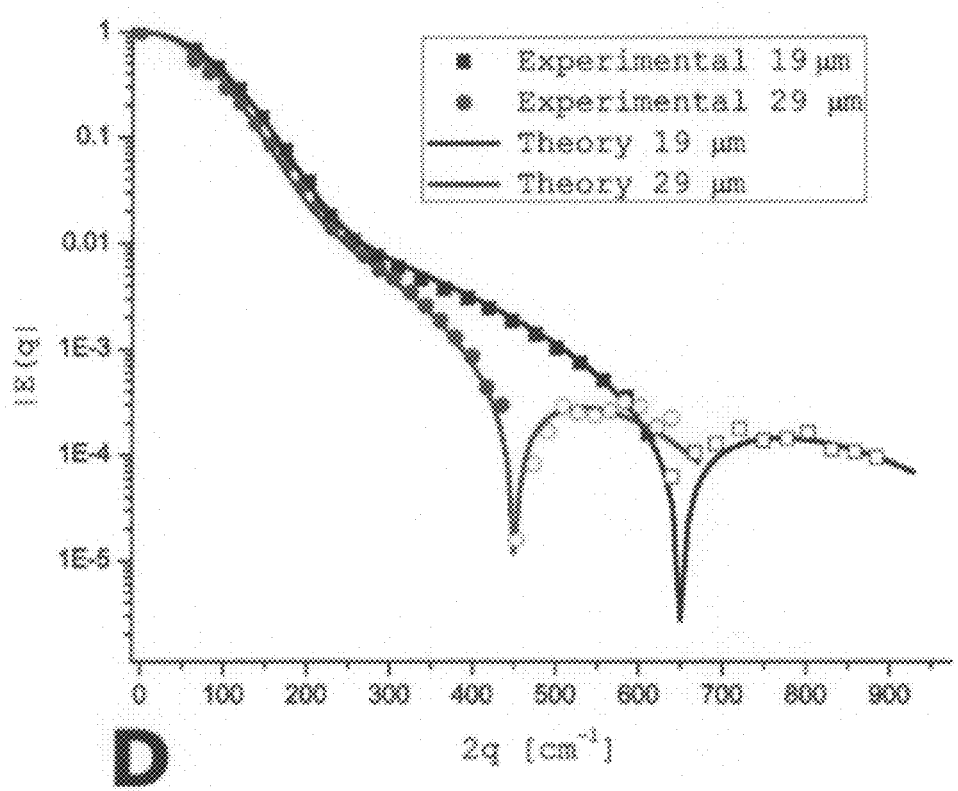
Figure 8E:
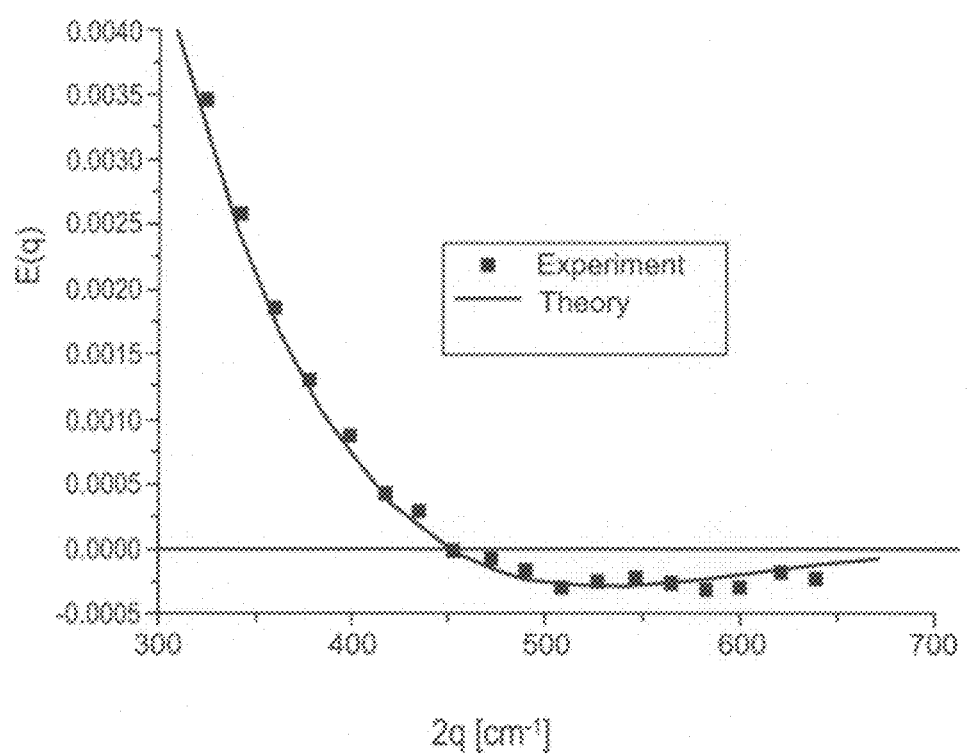

To show the sensitivity of the zero-crossings towards compartment size, similar experiments were performed on monodisperse porous media with a nominal ID of 19±1 µm (FIG. 8D). The zero-crossing is easily observed in this specimen, and the location of the zero-crossing is indeed at a higher q-value of 632 cm$^{-1}$ as expected from smaller pores. The profile was fitted to the theoretical function described in Shemesh et al. 2010, and the compartment size was calculated based on the fit. The calculated value was 19.65±0.20 µm, in excellent agreement with the nominal compartment size. The s-PFG, d-PFG and bp-s-PFG experiments did not yield any diffusion-diffraction minima for all specimens studied, and only a smooth, non-mono-exponential decays were observed, from which accurate microstructural information could not be directly inferred from the signal decay. Note that owing to the large internal gradients, the signal decays of both monopolar s- and d-PFG yield similar signal decays. By contrast, the signal decay induced by the bp-s-PFG of the present embodiments followed the expected smooth attenuation form for randomly oriented anisotropic pores.

Zero-Crossings in Polydisperse, Locally Anisotropic Pores

The results shown in FIG. 8 unequivocally demonstrate that bp-d-PFG sequence of the present embodiments can characterize randomly oriented monodisperse pores in terms of size, even in the presence of internal magnetic fields; however, most porous media are characterized also by size polydispersity, which in itself results in the loss of diffusion-diffraction troughs in s-PFG even when pores are coherently placed.

Figure 9:
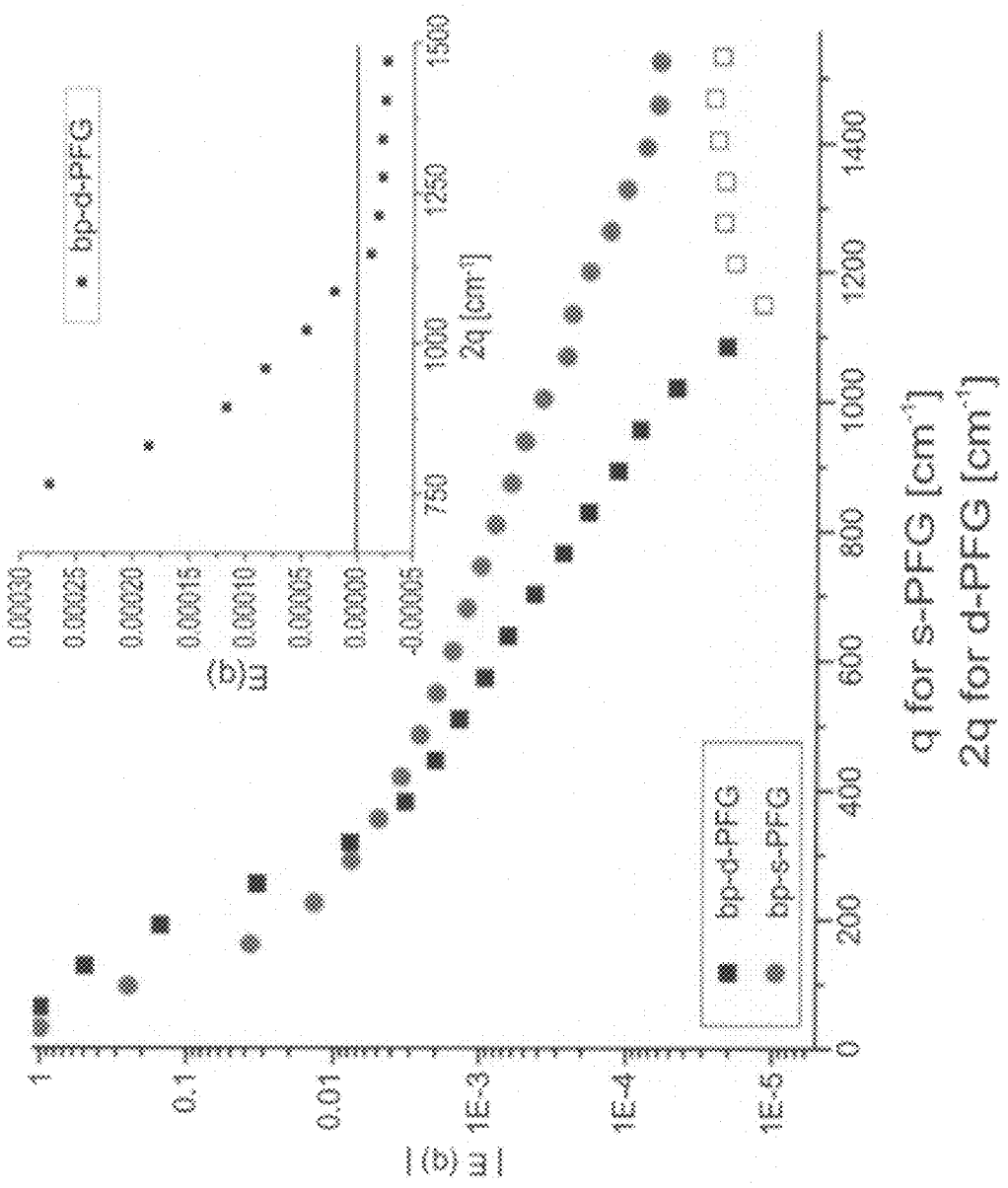
FIG. 9 shows as a function of the wavenumber as obtained in experiments performed according to some embodiments of the present invention on a sample with locally anisotropic pores having a size distribution of 14.9±4.6 μm.

To show that the bp-d-PFG sequence optionally and preferably can characterize porous media with all degrees of complexity (e.g., inhomogeneous field, randomly oriented anisotropic pores and size polydispersity) a polydisperse specimen having a mean±stdv of 14.9±4.6 µm was used. The specimen was cut to small pieces to achieve a random orientation of the locally anisotropic pores. The results of the bp-s-PFG and bp-d-PFG experiments on this specimen are shown in FIG. 9. Clearly, the bp-s-PFG does not yield diffusion-diffraction minima in this polydisperse porous medium. On the other hand the zero-crossing of the signal induced by the bp-d-PFG sequence of the present embodiments persists and is located at 2q=1150 cm$^{-1}$, corresponding to a compartment size of 10.6 µm, in good agreement with the nominal peak of the distribution, subject to a slight violation of the short gradient pulse (SGP) approximation. It is noted that as in the previous monodisperse specimens, zero-crossings were not be observed when d-PFG with monopolar gradients was performed (data not shown).

Extracting Compartment Shape in Randomly Oriented Locally Anisotropic Pores

Figure 10:
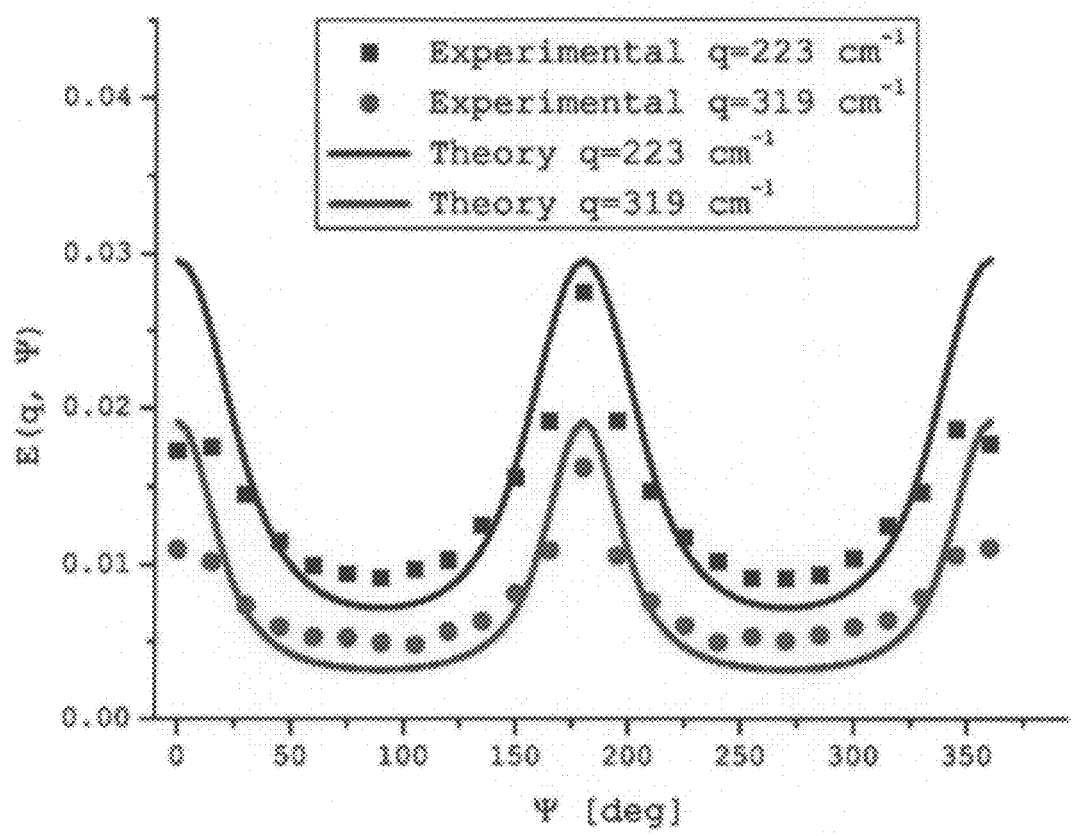
FIG. 10 shows signal profiles as a function of the angle between gradients as obtained in experiments performed according to some embodiments of the present invention on a sample having randomly oriented locally anisotropic pores.

To explore the local shape of the pores, randomly oriented cylindrical pores with nominal ID=10±1 µm were used and the bp-d-PFG sequence of the present embodiments was employed with long mixing times. FIG. 10 reveals the characteristic E(ψ) modulated curves, shown for two different q-values, indicating that pores are indeed non-spherical. The distinctive shape of the modulated E(ψ) curve is substantially different from what is expected from spherical pores (where E(ψ) is expected to be flat with no angular dependence at long $t_m$). Therefore, the curve allows inferring the cylindrical nature of the pores.

The theory and experiments are in good agreement, and a compartment dimension of 8.0±0.7 µm is extracted from fitting the angular dependence to the theory. The slight variation between theoretical and nominal size probably arises from incomplete suppression of susceptibility artifacts. It is noted this is the first experimental observation of compartment shape anisotropy, which provides unique information on pore shape non-invasively, unavailable by any other method. It is further noted that when the angular d-PFG experiment was performed with the d-PFG experiment with monopolar gradients, the E(ψ) profile was severely affected by the susceptibility effects, and the pore shape could not be obtained (data not shown).

Discussion

The present example demonstrates the ability of the technique according to some embodiments of the present invention to characterize morphological features even when many levels of complexity, including size polydispersity, random orientation of locally anisotropic pores, and magnetic field inhomogeneity, are present. Such a setting, although prominent in many porous media in a range of scientific disciplines ranging from biomedicine, geology and chemistry to material science, is extremely hard to characterize directly and non-invasively using conventional methods. Indeed, a method that would provide direct and robust characterization of pore shape and size would be advantageous over other model-dependant methodologies.

The technique employed in this example utilized bipolar gradients to overcome susceptibility induced effects within the porous medium, hybridized with the d-PFG methodology which can convey pore size and shape, even when specimens are heterogenic in size and orientation. Therefore, the bp-d-PFG methodology of the present embodiments uniquely yields non-invasive signatures for pore size and shape: the zero-crossings yield the pore size with very high accuracy; and the $E(\psi)$ profiles obtained in accordance with some embodiments of the present invention from angular bp-d-PFG pulse sequence enables one to non-invasively obtain a signature for compartment shape. In most applications, knowledge of these morphological features is sufficient to completely characterize the porous medium non-invasively, and provides a fingerprint for the specimen.

Even when the bipolar gradients were used in all s-PFG methodologies, no diffusion-diffraction patterns were observed, and the pore size from the signal decay could not be directly derive. In all specimens, the bp-s-PFG yielded an isotropic signal decay, thus the local pore anisotropy could not be inferred. Interestingly, in the randomly oriented specimens, which are characterized by large magnetic field inhomogeneity, the bp-s-PFG exhibited a signal decay which is much closer to its expected form than the s- or d-PFG experiments. This occurs since the susceptibility effects in these specimens are rather dramatic, and the internal gradients dominate the signal decay to a large extent when monopolar gradients are used.

The zero-crossings are a manifestation of restricted diffusion in d-PFG. Their robustness towards heterogeneity in both size and in shape arises from the fact that the signal is allowed to take a negative value in d-PFG NMR. Spins diffusing in compartments with different orientations contributes different signal values to the overall signal at each q-value. The fractional contribution of negative and positive signals leads to a cancellation of the signal at the q-value of the zero-crossing, and thus to the persistence of the zero-crossings in d-PFG NMR.

By contrast, the signal decay due to restricted diffusion in s-PFG is inherently always positive, and in the presence of randomly oriented anisotropic compartments, the additive nature of the signal simply smoothes the decay, leading to a loss of diffusion-diffraction minima. The robustness of d-PFG towards heterogeneity clearly makes it more suitable for obtaining sizes in heterogeneous specimens. But here, where severe magnetic susceptibility effects prevail, it is even more important to concatenate the d-PFG sequence with bipolar gradients. It is noted that in many realistic porous media, even the presence of restricted diffusion is hard to determine, especially if the signal decays rapidly due to susceptibility effects. Detection of zero-crossings is therefore advantageous since it provides unequivocal evidence for the presence of restricted diffusion within the porous medium.

The present example demonstrates that compartment shape anisotropy can be inferred from the $E(\psi)$ plots obtained using the bp-d-PFG sequence of the present embodiments with long mixing times. At long mixing times ($t_m$), the compartment shape anisotropy is decoupled from other mechanisms of anisotropy that are present, and the $E(\psi)$ profile can be used to differentiate between spherical and non-spherical pores: while $E(\psi)$ was predicted to be flat for spherical pores, characteristic modulated curves should be obtained for other compartment shapes.

The modulation in $E(\psi)$ that was clearly observed in the present example allowed inferring that the randomly oriented compartments were non-spherical. In other studies, a flat behavior of $E(\psi)$ was observed using d-PFG with long $t_m$ for a pack of coherently placed cylinders. These experiments were performed on a perimeter of a circle (since the pores were coherently placed and the angular d-PFG was performed in the plane perpendicular to the main axis of the pores), which has the same compartment shape anisotropy as a sphere. Therefore the flat angular dependence was consistent with that expected of diffusion in a sphere.

Other studies compared E(q) data at two different values of $\psi$ to infer on locally anisotropic motion. However, such measurements rely only on two points in the $E(\psi)$ curves that may be influenced, for example, by the susceptibility effects.

Thus, observing the full $E(\psi)$ modulation at different q-values in accordance with some embodiments of the present invention offers a much more robust and quantitative means for measuring compartment shape anisotropy, even at low q-values. In the present example, the full modulated bell shaped functions at long $t_m$ were observed for the first time, demonstrating that while overall diffusion is isotropic, the local anisotropy of the pores can be inferred directly from the $E(\psi)$ plots.

In addition to compartment shape, accurate compartment size can also be extracted from the $E(\psi)$ plots. Compartment shape anisotropy was observed in accordance with some embodiments of the present invention at low q-values, comparable with q-values in which DTI is routinely performed in the clinic. Thus, the present example demonstrates that the bp-d-PFG sequence of the present embodiments can be used in imaging, e.g., to create shape contrasts in CNS structures.

The random orientation of the compartments in this study resulted in relatively large susceptibility artifacts which were manifested in a relatively large line width (about 0.5 kHz). Susceptibility effects in porous materials such as rocks and other porous media are usually large, and can be used in accordance with some embodiments of the present invention as new sources of contrast in MRI of the CNS. The present inventors were showed that the bipolar d-PFG methodologies of the present embodiments can yield zero-crossings and bell shaped functions despite the large susceptibility effects in the sample.

Example 2

Apparent-Susceptibility Induced Anisotropy

Figure 11A:
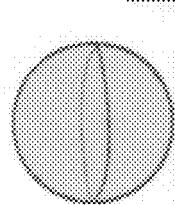
FIGS. 11A-D are schematic illustrations of a locally spherical pore (FIG. 11A), a locally anisotropic cylindrical pore (FIG. 11B), a three-dimensional region in which the locally anisotropic pores are randomly oriented (FIG. 11C), and a three-dimensional region in which the locally anisotropic pores are coherently placed.
Figure 11B:
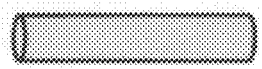

One of the most interesting features of pores embedded within porous media is their local shape and the way these pores are dispersed within the medium. Local pore shape can be considered as spherical or non-spherical (FIGS. 11A and 11B, respectively). However, while there is only one way to disperse spherical pores in a porous medium, locally cylindrical pores, for example, may be either randomly oriented (FIG. 11C) or coherently placed (FIG. 11D) within the porous medium.

Figure 11C:
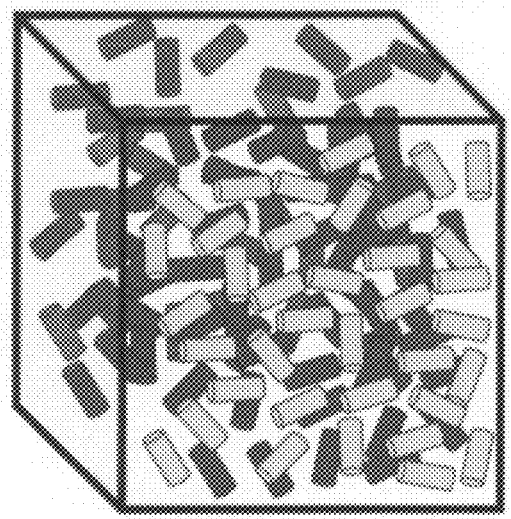
Figure 11D:
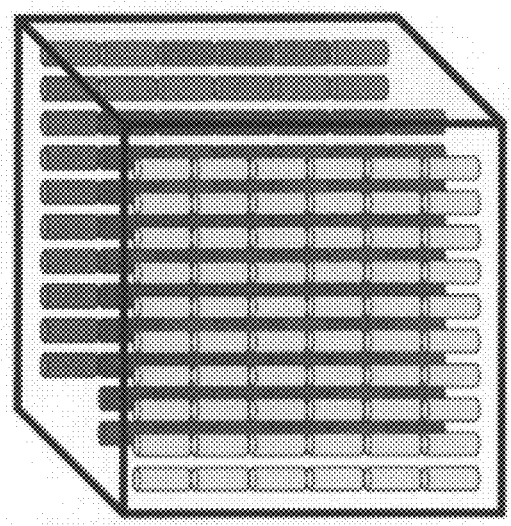

Conventional methods such as s-PFG methods are very limited in depicting the anisotropy, e.g., in the scenario shown in FIG. 11C, since it is extremely difficult to distinguish, for example, spheres from randomly oriented anisotropic pores, as well as to infer on restricted diffusion.

Many real porous media are heterogeneous in nature and are characterized by background gradients that arise from susceptibility differences within the specimen. The cross-terms between these background gradient and diffusion gradients affect the signal decay, and have been accounted for theoretically. The use of bipolar gradients can suppress, to different extent, the cross-terms.

In the present example, the signal decay in heterogeneous systems characterized by internal gradients was studied. As will be demonstrated below, the experimental data show that the bp-d-PFG sequence of the present embodiments provides novel microstructural information that is intractable using conventional s-PFG and d-PFG approaches. The experimental data further show that for controlled heterogeneous porous medium in which cylindrical pores are randomly oriented, the signal decay in both conventional PFG sequences exhibits the discovered aSIA effect which severely hinders the interpretation of diffusion data, leading to erroneous extraction of local pore anisotropy. As will be demonstrated below, the aSIA effects, originating from large magnetic field inhomogeneity, affect both conventional single- and d-PFG approaches. These aSIA effects can be suppressed by applying bipolar gradients. It will be demonstrated below that conventional s-PFG and d-PFG MR approaches do not provide sufficient information for directly extracting microstructural characteristics on pore size and shape in such heterogeneous specimens, and neither does bipolar-s-PFG MR. By contrast, the bp-d-PFG sequence of the present embodiments successfully provides MR signals from which such morphological features can be extracted.

Experimental

Specimen Preparation

Porous Media

Hollow microcapillaries with well defined inner diameter (ID) (PolyMicro Technologies, Phoenix Ariz., USA) were manually cut to very small pieces (<0.5 cm) or crushed by mechanical force to very small particles, and immersed in distilled water for several days, for filling. The resultant porous media was poured into an 8 or in some cases 10 mm NMR tube containing Fluorinert (Sigma-Aldrich, Rehovot, Israel). The entire water signal arises from diffusion which occurs strictly in the intra-tubular space since polarity differences between the heavier Fluorinert and water precludes exchange between compartments, and the density differences keep any extra-tubular water in the top part of the NMR tube, which was located outside the RF coils.

Quartz Sand Specimen

A specimen of clean coarse Quartz sand was crushed to smaller particles. The sand was poured to a 10 mm NMR tube, which was then filled with distilled water and the NMR tube was sealed. The specimen was allowed to equilibrate for several days prior to the NMR experiment.

Emulsion System

The emulsion system was prepared by adding 40 μl of Triton X-100 (Sigma Aldrich, Rehovot, Israel) to 1980 μl of $H_2O$, and subsequently adding 1980 μl of Toluene (Sigma Aldrich, Rehovot, Israel) to the mixture at room temperature. The mixture was vortexed for 30 seconds, and the resulting emulsion was allowed to settle overnight prior to NMR experiments.

Yeast Cells

The yeast were hydrated with Phosphate-Buffer-Saline (PBS) (Sigma-Aldrich, Rehovot, Israel), then centrifuged for 10 minutes at 1000 rpm. The yeast were then suspended in paraformaldehyde (Sigma-Aldrich, Rehovot, Israel) fixative for 90 minutes, then washed twice with PBS. After the second wash, the cells were centrifuged again for 10 minutes and at 1000 rpm. The supernatant was removed and the yeast cells were suspended in a small amount of PBS, which was poured to an 8 mm NMR tube. The fixated cells were allowed to settle overnight at 4° C., and the water that collected above the yeast was removed prior to the NMR experiments.

NMR Experiments

The NMR tube containing the porous medium was placed in a Bruker 8.4 T NMR spectrometer equipped with a Micro5 probe capable of producing nominal pulsed gradients up to 1900 mT/m in each direction. The temperature was kept constant throughout the experiments.

Randomly Oriented Pores with ID=29±1 μm

Single-PFG and bp-s-PFG were conducted with the sequences shown in FIGS. 1 and 2A respectively, with the following parameters: $\Delta/\delta=250/3$ ms, 32 q-values were collected with $G_{max}$ of 600 mT/m, resulting in a maximum q-value of 766 cm$^{-1}$. The number of scans was set to 32.

Conventional d-PFG sequence (FIG. 3B) and the bp-d-PFG sequence of the present embodiments (FIG. 4C) with $\Delta_1=\Delta_2=250$ ms, $\delta_1=\delta_2=\delta_3=3$ ms and $t_m=0$ ms, were applied. A total of 32 points were collected with $G_{max}=300$ mT/m resulting in a $q_{max}$ of 383 cm$^{-1}$.

Randomly Oriented Pores with ID=10±1 μm

To show compartment shape anisotropy, conventional d-PFG sequence (FIG. 3A) and the bp-d-PFG sequence of the present embodiments (FIG. 4A) with $\Delta_1=\Delta_2=150$ ms, $\delta_1=\delta_2=3$ ms and $t_m=18$ ms, were applied. Briefly, $\underline{G}_1$ was fixed in the x-direction, and the orientation of $\underline{G}_2$ was varied in 25 equal steps along 360° in the X-Y plane (perpendicular to the direction of $B_0$). In these experiments $|\underline{G}_1|=|\underline{G}_2|$.

Experiments on the Emulsion System

Conventional d-PFG sequence (FIG. 3B) and the bp-d-PFG sequence of the present embodiments (FIG. 4C) with $\Delta_1=\Delta_2=200$ ms, $\delta_1=\delta_2=\delta_3=3$ ms and $t_m=0$ ms, were applied. $\underline{G}_1$ was fixed in the x-direction, and the orientation of $\underline{G}_2$ was varied in 25 equal steps along 360° in the X-Y plane (perpendicular to the direction of $B_0$). In these experiments $|\underline{G}_1|=|\underline{G}_2|$.

Quartz Sand Experiments

Conventional d-PFG sequence (FIG. 3B) and the bp-d-PFG sequence of the present embodiments (FIG. 4C) with $\Delta_1=\Delta_2=50$ ms, $\delta_1=\delta_2=\delta_3=3$ ms and $t_m=0$ ms, were applied. $\underline{G}_1$ was fixed in the x-direction, and the orientation of $\underline{G}_2$ was varied in 25 equal steps along 360° in the X-Y plane (perpendicular to the direction of $B_0$). In these experiments $|\underline{G}_1|=|\underline{G}_2|$.

Emulsion Experiments

Conventional d-PFG sequence (FIG. 3B) and the bp-d-PFG sequence of the present embodiments (FIG. 4C) with $\Delta_1=\Delta_2=50$ ms, $\delta_1=\delta_2=\delta_3=3$ ms and $t_m=0$ ms, were applied. $\underline{G}_1$ was fixed in the x-direction, and the orientation of $\underline{G}_2$ was varied in 25 equal steps along 360° in the X-Y plane (perpendicular to the direction of $B_0$). In these experiments $|\underline{G}_1|=|\underline{G}_2|$.

Yeast Cells

Conventional d-PFG sequence (FIG. 3B) and the bp-d-PFG sequence of the present embodiments (FIG. 4C) with $\Delta_1=\Delta_2=200$ ms, $\delta_1=\delta_2=\delta_3=3$ ms and $t_m=0$ ms, were applied. $\underline{G}_1$ was fixed in the x-direction, and the orientation of $\underline{G}_2$ was varied in 25 equal steps along 360° in the X-Y plane (perpendicular to the direction of $B_0$). In these experiments $|\underline{G}_1|=|\underline{G}_2|$. The $E(\psi=180°$ value for the conventional experiment was replaced with the average of the two neighboring points owing to a signal fluctuation.

Results

The results are shown in FIGS. 12A-15C.

Figure 12A:
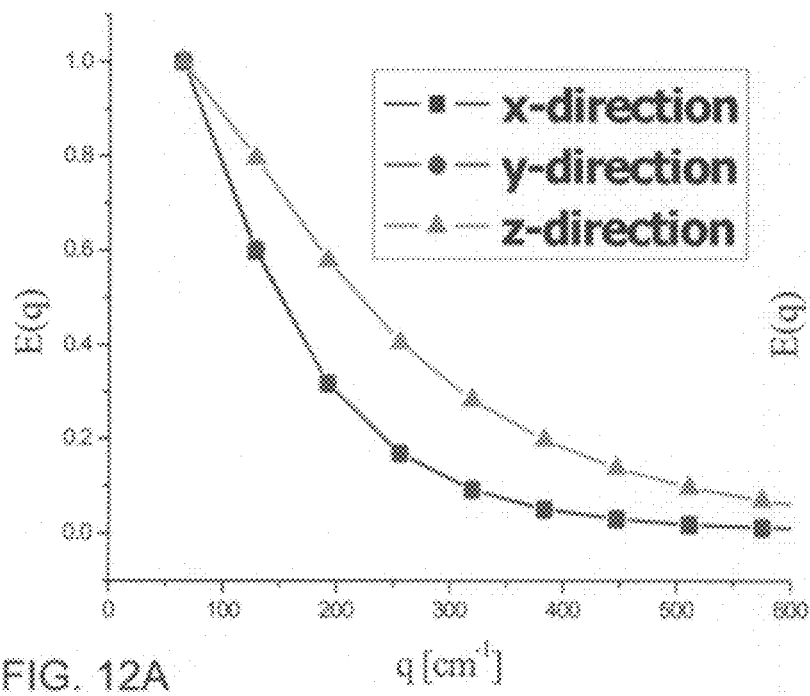
FIGS. 12A-B show signal profiles as a function of the wavenumber, as obtained by applying an s-PFG sequence (FIG. 12A) and a single-pair bipolar PFG sequence (FIG. 12B), to a sample having randomly oriented pores with size distribution of 29±1 μm.

FIG. 12A shows the signal decay from the x-, y- and z-directions in conventional s-PFG experiments (sequence shown in FIG. 1) conducted on a controlled porous medium comprised of randomly oriented cylindrical pores having nominal ID of 29±1 μm (depicted schematically in FIG. 11C). The linewidth in this specimen was about 0.5 kHz. Since the pores are completely randomly oriented, the diffusion propagators are averaged along all directions and the s-PFG signal decay should appear isotropic. However, as shown clearly in FIG. 12A, the signal decay is anisotropic, even at low q-values. This observation may lead to the erroneous conclusion that in this specimen, pores are coherently placed. This is a manifestation of the discovered aSIA effect.

Figure 12B:
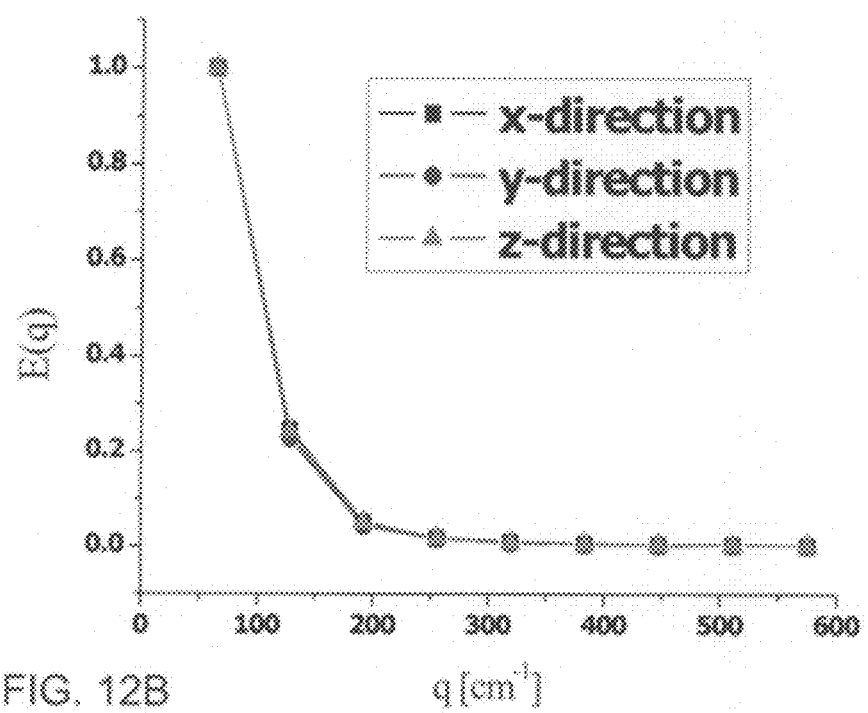

When the corresponding bp-s-PFG experiments (sequence shown in FIG. 2A) were performed, the signal decay appeared isotropic (FIG. 12B). However, obtaining such an isotropic profile exemplifies the inability of bp-s-PFG to accurately depict the local morphological features in such a randomly oriented specimen since it is impossible to determine whether the porous medium has spherical pores or locally anisotropic randomly oriented pores. In fact, it is difficult even to infer on the presence of restricted diffusion from the bp-s-PFG signal decay.

In the present example a conventional d-PFG sequence (FIG. 3B) and the inventive bp-d-PFG sequence (FIG. 4C) were applied to a controlled porous specimen with randomly oriented cylindrical pores having an ID of 10±1 μm.

Figures 13A, 13B:
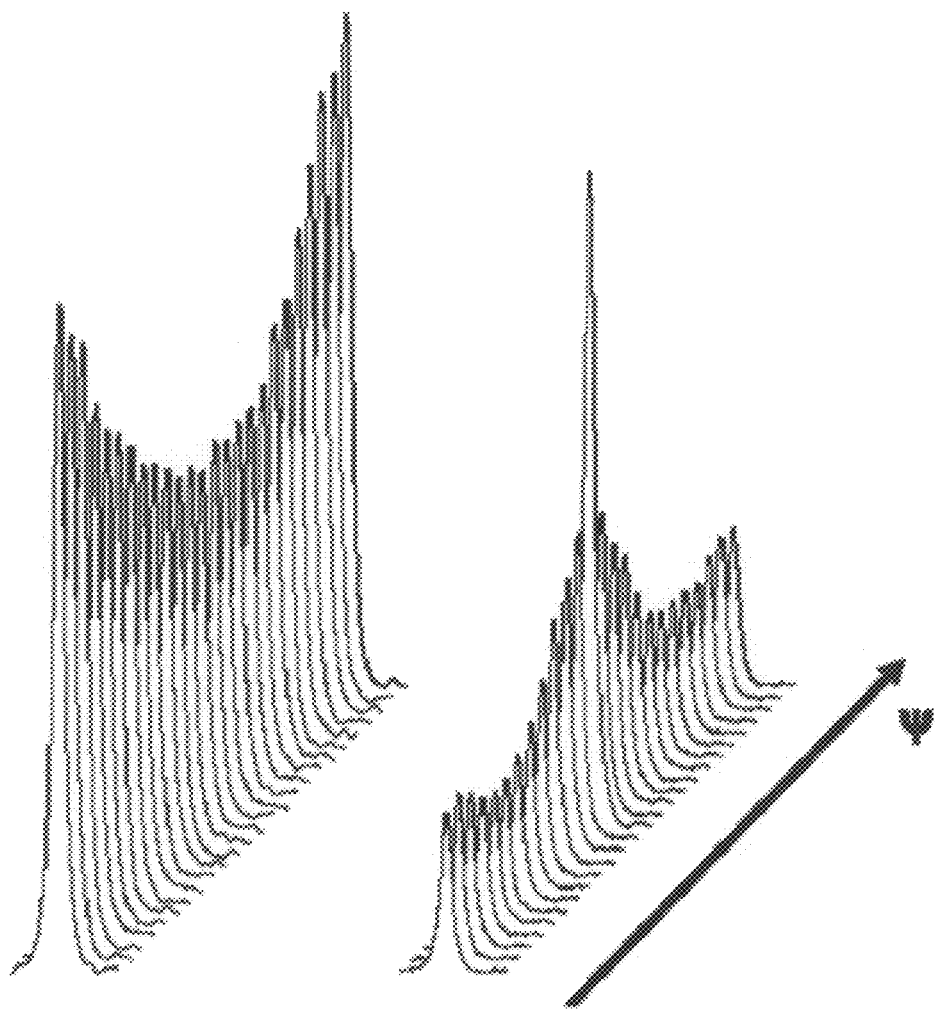
FIGS. 13A-C show signal profiles as a function of the angle between gradients, as obtained by applying a d-PFG sequence (FIG. 13A and open symbols in FIG. 13C) and a sequence according to some embodiments of the present invention (FIG. 13B and filled symbols in FIG. 13C), using a zero mixing time to a randomly oriented locally cylindrical pores with a size distribution 10±1 μm.

FIG. 13A shows a stackplot of the NMR signal as function of the angle $\psi$ at $2q=255$ cm$^{-1}$ (where $|q|=|q_1|=|q_2|$). By contrast with theoretical predictions, the angular dependence arising from the conventional d-PFG experiment appears inverted: the signal diminishes between $\psi=0°$-180°, then rises back towards its original value. This is the manifestation of the discovered aSIA effect in the signal decay of conventional d-PFG.

Figure 13C:
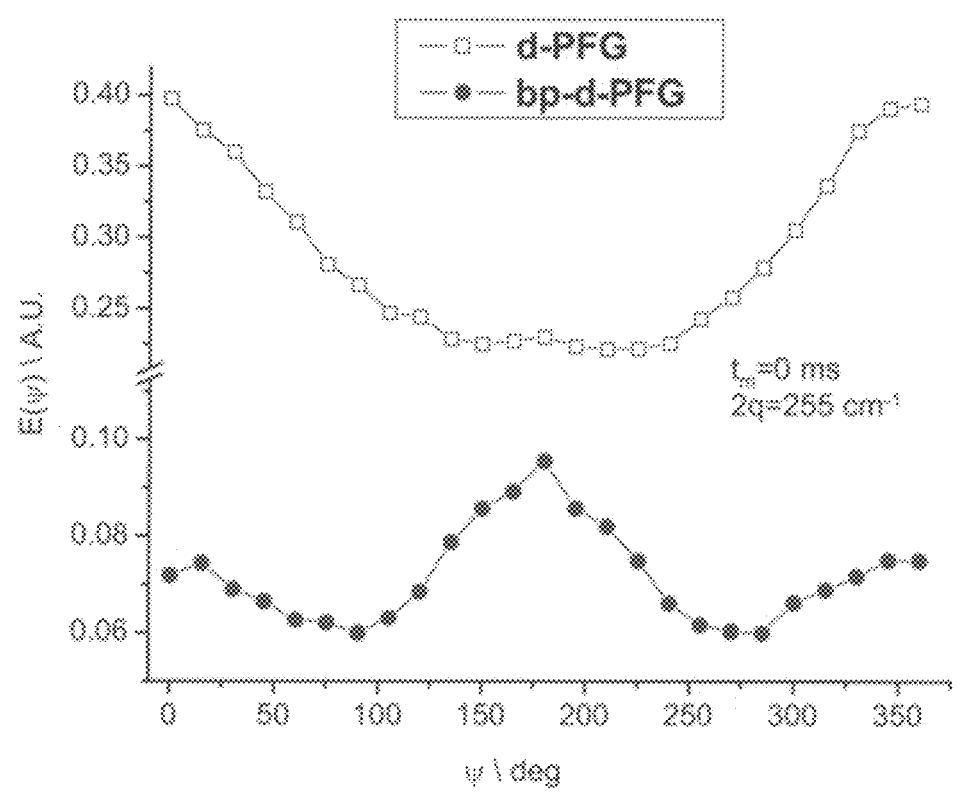

When the bp-d-PFG of the present embodiments was applied to the same system, the aSIA was significantly suppressed, and the expected angular profile was obtained (FIG. 13B). FIG. 13C shows these phenomena in the $E(\psi)$ plots. These results demonstrate that the bp-d-PFG sequence of the present embodiments uniquely depicted the presence of restricted diffusion within the specimen, from which accurate pore size can also be obtained.

The theory predicts the $E(\psi)$ profile at long $t_m$ to be flat for spherical pores, and modulated for non-spherical pores.

Figure 14:
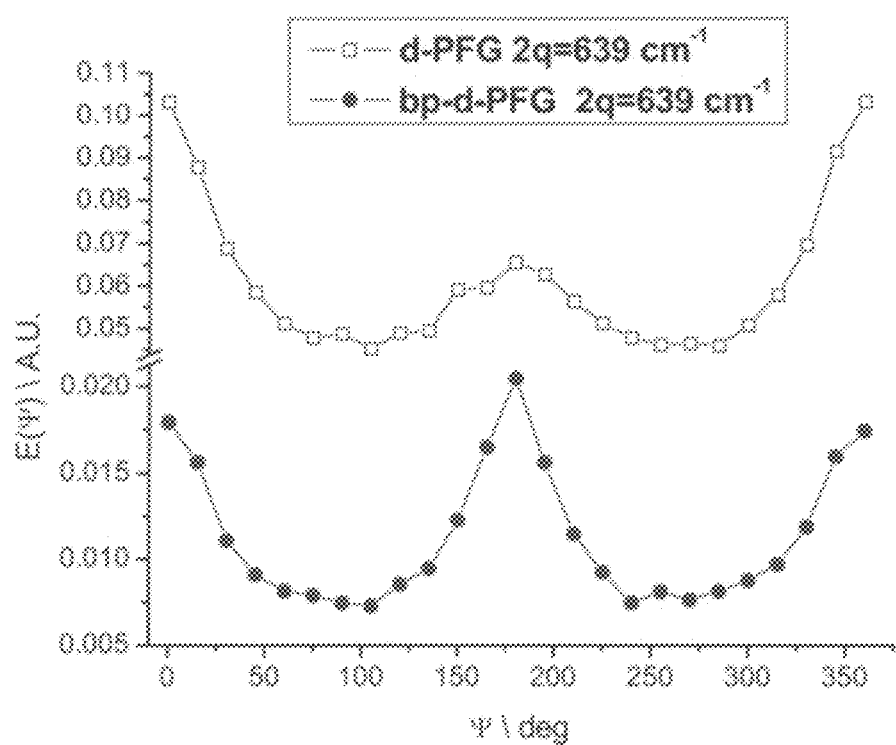
FIG. 14 shows signal profiles as a function of the angle between gradients, as obtained by applying a d-PFG sequence (open symbols) and a sequence according to some embodiments of the present invention (filled symbols), using a mixing time of 18 ms, to a randomly oriented locally cylindrical pores with a size distribution 10±1 μm.

FIG. 14 shows the $E(\psi)$ plots at $2q=639$ cm$^{-1}$ and at a long $t_m$ of 18 ms for both conventional d-PFG (FIG. 3A) and the inventive bp-d-PFG (FIG. 4A) sequences applied to the same controlled porous medium. At $t_m=18$ ms, local compartment shape cannot be inferred from the conventional angular d-PFG experiments, since the susceptibility effects again yield an inverted angular dependence. By inspecting the $E(\psi)$ profile arising from the bp-d-PFG sequence of the present embodiments it was inferred that the pores are locally not spherical. The modulated bell shaped function attains its expected form. These results demonstrate that the bp-d-PFG sequence of the present embodiments provide information on local compartment anisotropy, microstructural information that is not accessible from none of the conventional s-PFG, bp-s-PFG (as the signal decay is isotropic), and d-PFG sequences.

To demonstrate the utility of angular bp-d-PFG of the present embodiments to extract information from realistic heterogeneous specimens in diverse applications, this methodology was applied in accordance with some embodiments of the present invention to Quartz sand, emulsions, and biological cells.

First, the angular bp-d-PFG methodology was used to study a water-saturated Quartz sand specimen, where very large internal gradients prevail; indeed the water linewidth was about 1.2 kHz.

Figure 15A:
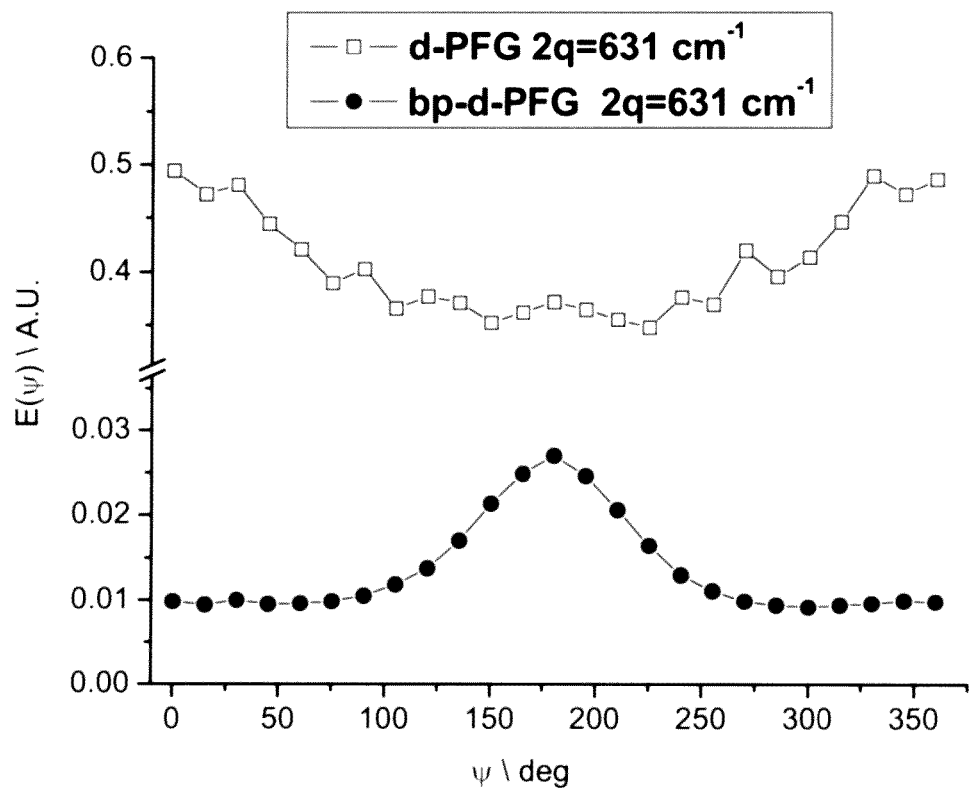
FIGS. 15A-C show signal profiles as a function of the angle between gradients, as obtained by applying a d-PFG sequence (open symbols) and a sequence according to some embodiments of the present invention (filled symbols), to quartz sand (FIG. 15A), an emulsion system (FIG. 15B), and yeast cells (FIG. 15C).

FIG. 15A shows $E(\psi)$ as obtained from the conventional d-PFG and the inventive bp-d-PFG sequences at $2q=631$ cm$^{-1}$. Using the conventional d-PFG sequence, the presence of restricted diffusion cannot be inferred. On the other hand, the angular bp-d-PFG technique of the present embodiments revealed a pronounced bell shaped function, from which the presence of restricted diffusion within the pores and interstices of the sand grains can be obtained. Thus, the sequence of the present embodiments allows extracting information regarding the specimen microstructure. This is the first observation of a bell-shaped function in sand specimen and it implies that diffusion is non-Gaussian even at relatively low q-values for the experimental parameters used since bell-shaped functions at $t_m=0$ ms will only arise from restricted diffusion, as opposed to multi-Gaussian processes.

Diffusion NMR is particularly useful for the analysis of emulsion systems. In the present example, a conventional d-PFG sequence and the bp-d-PFG sequence of the present embodiments were applied to an emulsion of toluene in water, where the linewidth was about 30 Hz.

Figure 15B:
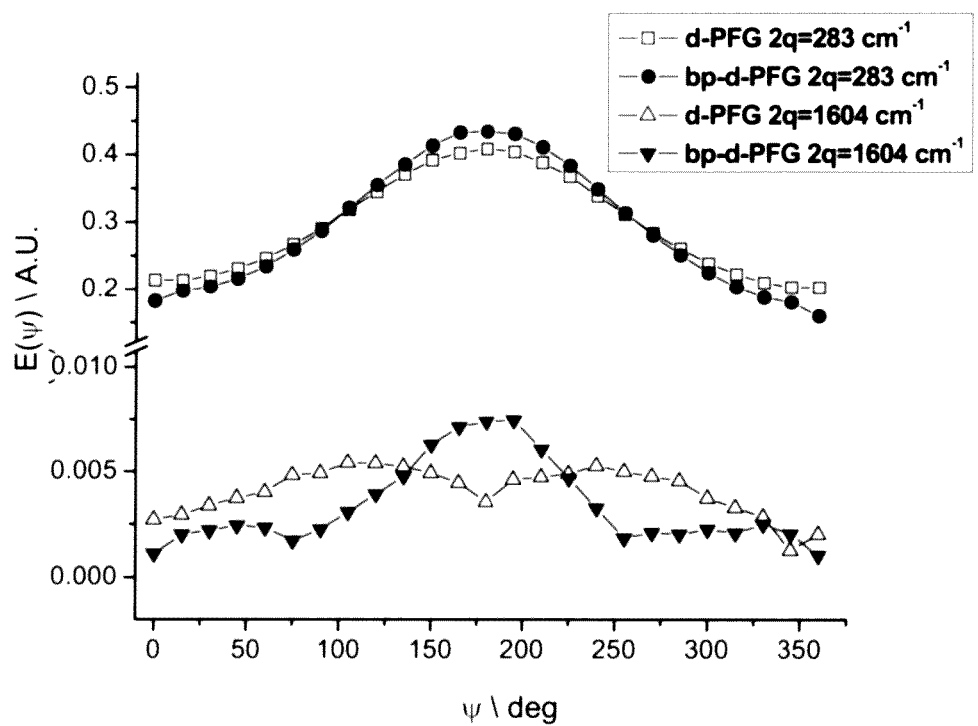

The results are shown in FIG. 15B, which depicts $E(\psi)$ for two q-values. At low q-values, the aSIA effect is less pronounced in this specimen, and both methodologies convey the presence of restricted diffusion. On the other hand, at higher q-values, the conventional d-PFG sequence yields became distorted at $\psi=180±60°$. Therefore, no accurate microstructural information can be obtained at these q-values. It was found by the present inventors that the bp-d-PFG sequence of the present embodiments has corrected the aSIA effect.

To further test the robustness and sensitivity of the $E(\psi)$ profile to systems where susceptibility differences are smaller than in chemical applications, the same experiments were performed on yeast cells.

Fixated *S. Cerevisiae* yeast cells were found to be mostly spherical under light microscopy, and are therefore expected to produce an $E(\psi)$ angular dependence that resembles a non-modulated bell-shaped function, were used. The conventional d-PFG sequence (FIG. 3B) and the inventive bp-d-PFG sequence (FIG. 4C) were applied to the yeast specimen. The line width in this specimen was about 30 Hz.

Figure 15C:
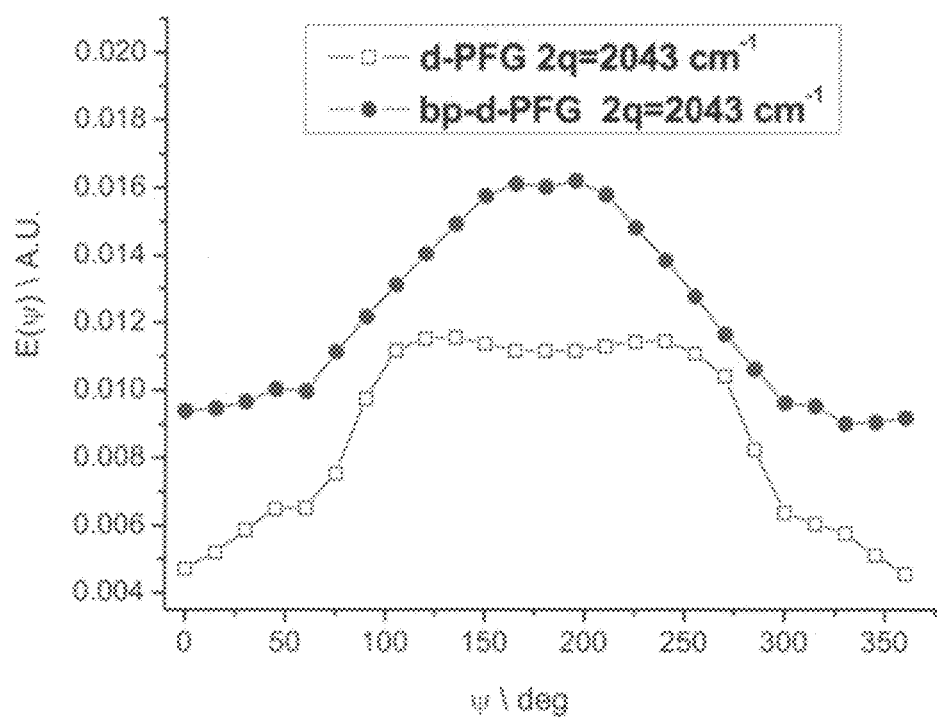

FIG. 15C shows the angular dependence of both methodologies from this specimen at $2q=2043$ cm$^{-1}$. The angular dependence in conventional d-PFG became distorted at $\psi=180\pm60°$, with a plateau-like modulation. This plateau became more pronounced with increasing q-values (data not shown). The bp-d-PFG of the present embodiments, on the other hand, revealed a bell-shaped $E(\psi)$ profile which is expected at $t_m=0$ ms for such spherical compartments, and the plateau-like artifacts disappeared.

Conclusions

This example demonstrated that the bp-d-PFG sequence of the present embodiments provides important microstructural information in heterogeneous systems totally noninvasively and, in some cases, using relatively weak gradients. The present example demonstrated that internal magnetic fields in heterogeneous porous media, may result in misinterpretations of anisotropy within the specimen when conventional d-PFG sequence is employed, and may prohibit accurate size extraction. The present example demonstrated that aSIA can be avoided by using the bp-d-PFG sequence in heterogeneous specimens from porous media, Quartz sand and emulsions to biological specimens.

This example demonstrated the usefulness of the present embodiments for studying diverse types of porous media for obtaining novel microstructural insight on pore morphology.

Example 3

Nerve Tissues

Figure 16A:
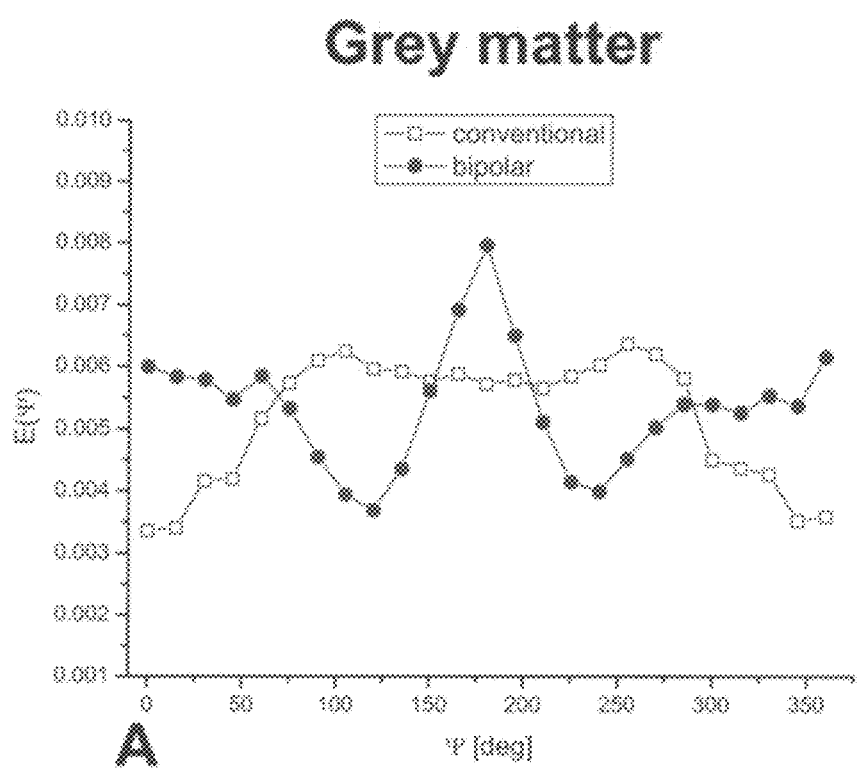
FIGS. 16A-B show signal profiles as a function of the angle between gradients, as obtained by applying a d-PFG sequence (open squares) and a sequence according to some embodiments of the present invention (filled circles), to grey (FIG. 16A) and white (FIG. 16B) matter tissues.
Figure 16B:
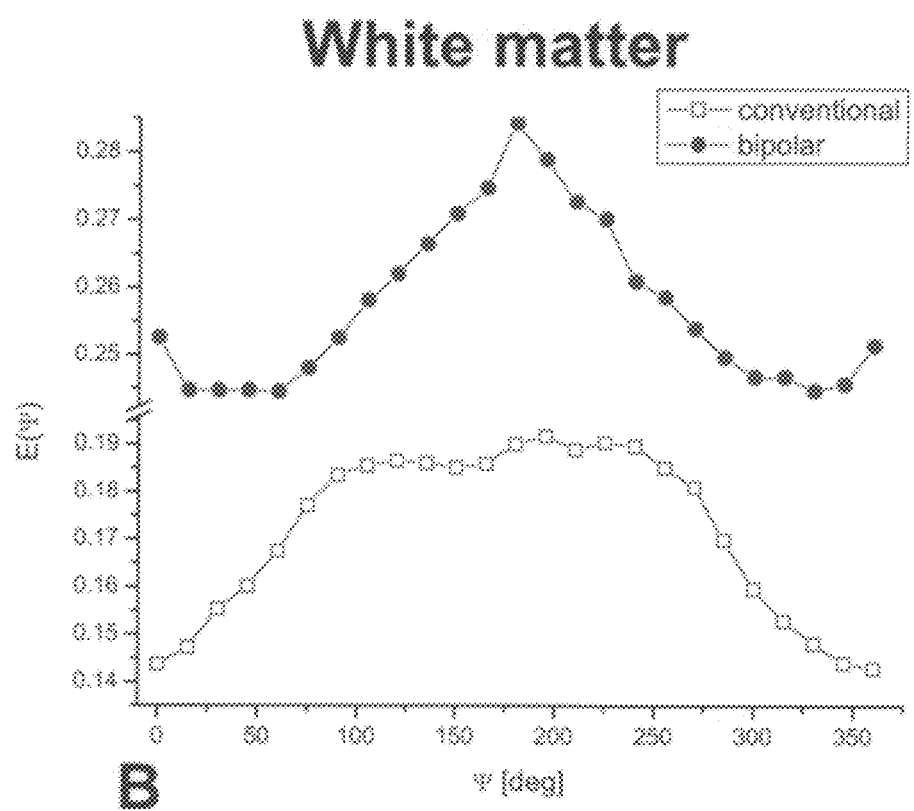

FIGS. 16A and 16B show $E(\psi)$ profiles obtained from an MR signal received from grey (FIG. 16A) and white (FIG. 16B) matter tissues, in response to the conventional d-PFG sequence shown in FIG. 3B (squares) and the sequence of the present embodiments (circles) shown in FIG. 4C. The experimental parameters for both cases were: $2q=2043$ $cm^{-1}$, $t_m=0$ ms and $\Delta_1=\Delta_2=50$ ms and $\delta_1=\delta_2=\delta_3=3$ ms.

For the conventional sequence, the $E(\psi)$ profiles show an erroneous angular dependence both for the grey matter and the white matter tissues.

On the other hand, the sequence of the present embodiments provided the expected angular dependence for both randomly oriented cells (grey matter) and coherently placed axons (white matter).

This example demonstrates the ability of the present embodiments to provide microstructural information such as cell shape, size and orientation distribution even in highly heterogeneous biological tissues such as neuronal tissues.

Example 4

Rocks

Figure 17A:
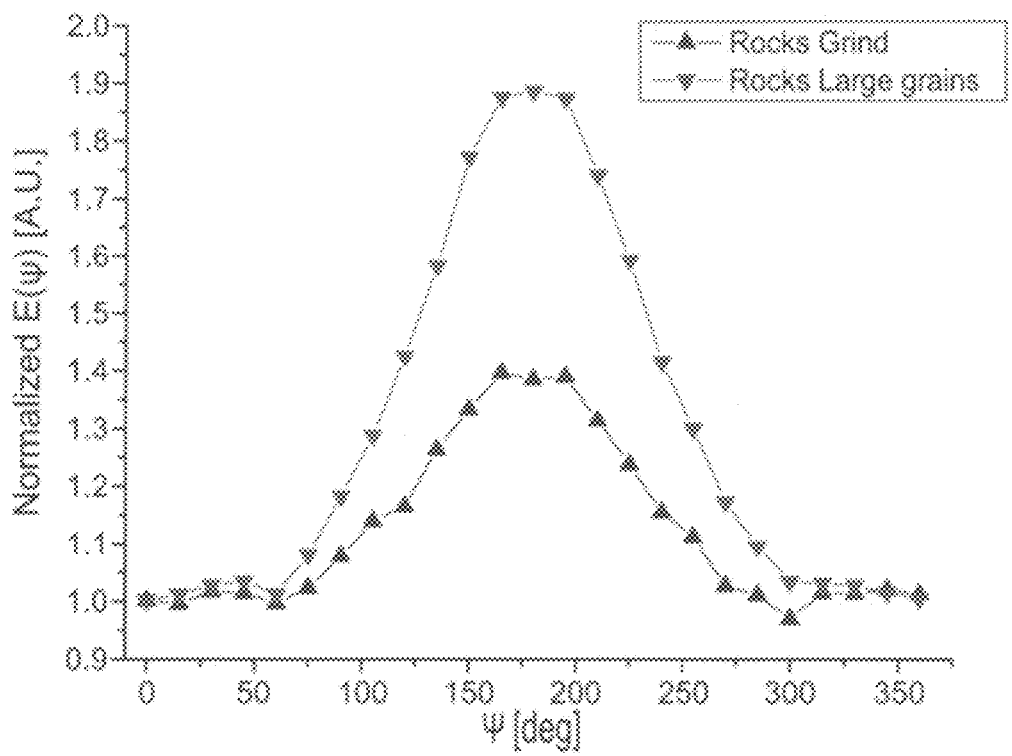
FIGS. 17A-B show results of experiments performed in accordance with some embodiments of the present invention on quartz sand specimens (FIG. 17A) and a rock specimen (FIG. 17B).

FIG. 17A shows results of experiments performed in accordance with some embodiments of the present invention on two different Quartz sand specimens, containing grains of different sizes. For both experiments, the bp-d-PFG sequence of the present embodiments was employed (sequence shown in FIG. 4C). The experimental parameters for both cases were: $2q=393$ $cm^{-1}$, $t_m=0$ ms and $\Delta_1=\Delta_2=50$ ms and $\delta_1=\delta_2=\delta_3=3$ ms. The signature for the pore size as can be inferred from the sharpness of the angular dependence.

It is noted that conventional d-PFG does not convey any meaningful microstructural information (data not shown).

Figure 17B:
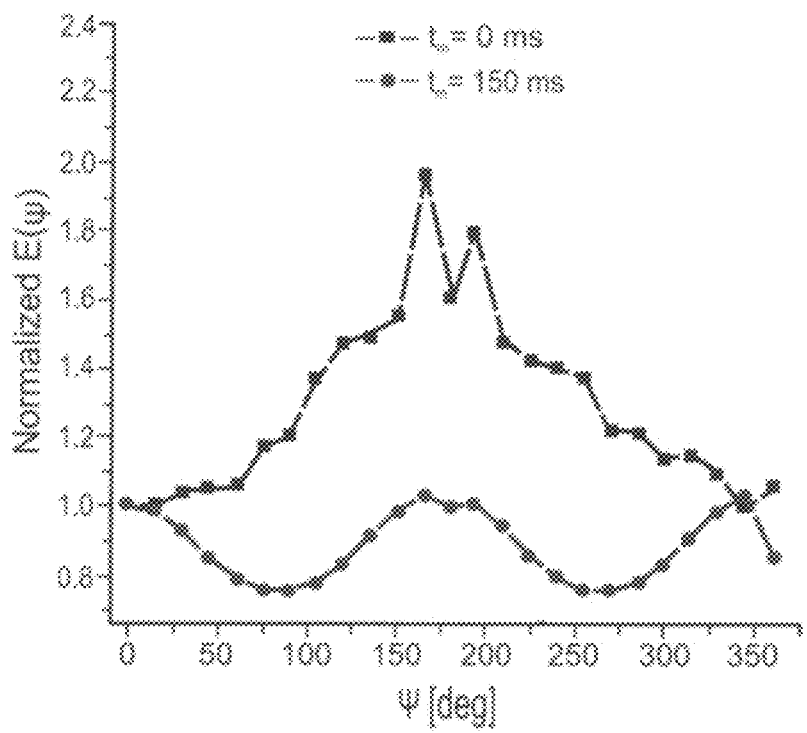

FIG. 17B shows results of experiments performed in accordance with some embodiments of the present invention on a rock specimen. In these experiments, the diffusing fluid (in, this case, water) is confined within porous networks of the rock. The inventive bp-d-PFG sequences shown in FIGS. 4A and 4C were used, with $t_m=150$ ms and $t_m=0$ and $\delta_1=\delta_2=3$ ms, and $\delta_1=\delta_2=\delta_3=3$ ms, respectively.

The results show the characteristic signatures for both microscopic anisotropy (from the bell-shaped angular dependence at zero mixing time, black boxes) and compartment shape anisotropy (from the signal oscillation at the longer mixing time, red circles). It is noted that these two unique parameters cannot be inferred from conventional s-PFG (FIG. 1), bp-s-PFG (FIG. 2A) or conventional d-PFG sequences (FIGS. 3A-B) (data not shown).

Example 5

Biological Cells

Figure 18A:
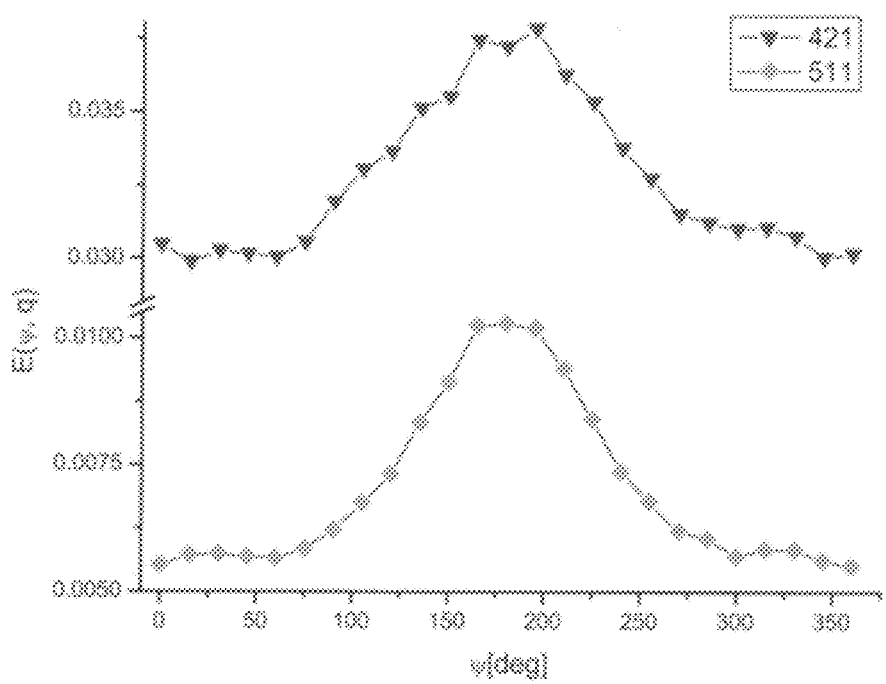
FIGS. 18A-C show results of experiments performed in accordance with some embodiments of the present invention on different cell types: Cyanobacteria (FIG. 18A), stem cells (FIG. 18B) and cancer cells (FIG. 18C).
Figure 18B:
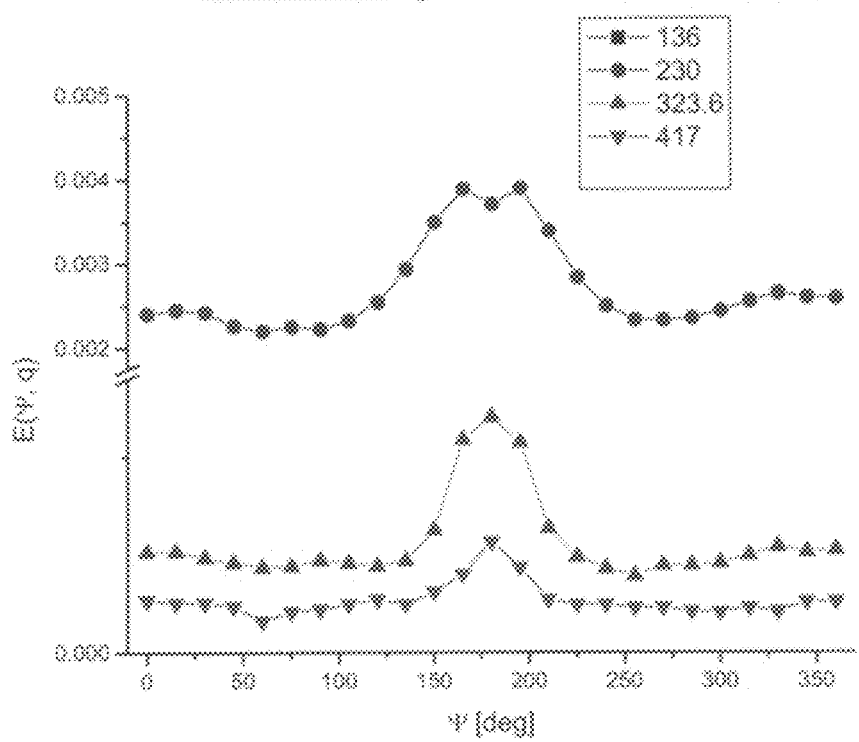
Figure 18C:
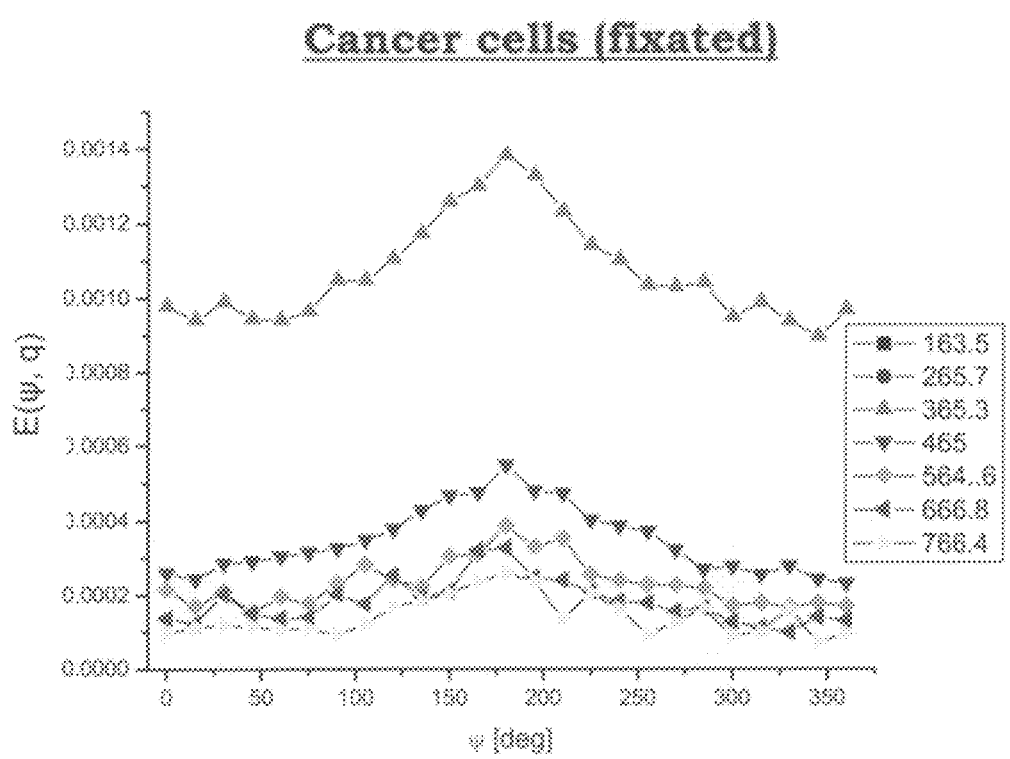

FIGS. 18A-C show results of experiments performed in accordance with some embodiments of the present invention on different cell types: Cyanobacteria (FIG. 18A), stem cells (FIG. 18B) and cancer cells (FIG. 18C). The bp-d-PFG sequence of the present embodiments was applied for all three cell types. The sequence used is shown in FIG. 4C. The experimental parameters were $t_m=0$ ms and $\Delta_1=\Delta_2=50$ ms and $\delta_1=\delta_2=\delta_3=3$ ms. The 2q values are specified in FIGS. 18A-C.

The results demonstrate that of the bp-d-PFG sequence of the present embodiments can be utilized in analysis of including cell cultures. The angular dependence is clearly seen, demonstrating that microscopic anisotropy exists in these cells, which can be used to extract compartment size.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of magnetic resonance analysis of a sample, comprising:

applying to the sample a plurality of pairs of bipolar gradient pulse subsequences, wherein each bipolar gradient pulse subsequence of each pair comprises:

a first gradient pulse corresponding to a first activation of a gradient coil at a first amplitude for a first period of time, a second gradient pulse corresponding to a second activation of said gradient coil at a second amplitude for a second period of time, and a radiofrequency sequence in which both said first gradient pulse and said second gradient pulse are embedded, wherein said first and said second activations are along a gradient direction specific to said pair, wherein said first and second amplitudes are of opposite polarity, and
wherein, in each pair, there is at least one radiofrequency pulse between every two successive gradient pulses;
acquiring a magnetic resonance signal from the sample;
analyzing the signal; and
issuing a report regarding said analysis.

2. The method according to claim 1, wherein each pair of bipolar gradient pulse subsequences is characterized by a different gradient direction.

3. The method according to claim 1, wherein said plurality of pairs is two pairs.

4. The method according to claim 3, further comprising performing a series of experiments, each experiment being characterized by a different angle ω between the respective gradient directions of said bipolar gradient pulse subsequences.

5. The method of claim 4, further comprising analyzing signal profiles as a function of said angle so as to extract at least one of: shape information and size information from the sample.

6. The method of claim 5, further comprising generating an estimate of eccentricity distribution of restricted compartments in the sample, thereby providing said shape information.

7. The method according to claim 1, wherein the sample is a porous sample.

8. The method according to claim 1, further comprising analyzing said signal as a function of a magnetic resonance wavenumber so as to generate an estimate of a size distribution of restricted compartments in the sample.

9. The method according to claim 1, wherein the sample is characterized by NMR line width of at least 10 Hz.

10. The method according to claim 1, wherein the sample is a porous sample characterized by an average pore size of less than 50 microns, with a standard deviation which is at least 3%.

11. The method according to claim 1, wherein the sample is a porous sample characterized by an average pore size of less than 50 microns and said bipolar gradient pulse subsequences are devoid of any gradient pulse having a magnitude which is above than 100 gauss/cm.

12. The method according to claim 1, wherein the sample comprises at least one object selected from the group consisting of a sediment, a rock, a heterogeneous catalyst, a porous material, a porous polymers, an emulsion product, a biological cell, a tissue, a central-nervous-system tissue, quartz sand and a yeast cell.

13. The method according to claim 1, further comprising using said magnetic resonance signal from the sample for imaging the sample.

14. The method according to claim 1, wherein a mixing time between bipolar gradient pulse subsequences of said pair is selected to allow determination of a shape of pores in said sample.

15. The method according to claim 1, wherein an intensity of said bipolar gradient pulse subsequences is selected to allow identification of at least one of a predetermined compartment shape, a predetermined compartment size and a predetermined compartment organization.

16. The method according to claim 1, wherein said bipolar gradient pulse subsequences are embedded in radiofrequency sequences selected from the group consisting of spin echo sequences, stimulated echo sequences, gradient echo sequences and any combination thereof.

17. A system for magnetic resonance analysis, comprising;

a radiofrequency system configured for generating a plurality of pairs of bipolar gradient pulse subsequences, and acquiring magnetic resonance signals from the sample,
wherein each bipolar gradient pulse subsequence of each pair comprises:
a first gradient pulse corresponding to a first activation of a gradient coil at a first amplitude for a first period of time,
a second gradient pulse corresponding to a second activation of said gradient coil at a second amplitude for a second period of time, and
a radiofrequency sequence in which both said first gradient pulse and said second gradient pulse are embedded,
wherein said first and said second activations are along a gradient direction specific to said pair,
wherein said first and second amplitudes are of opposite polarity, and
wherein, in each pair, there is at least one radiofrequency pulse between every two successive gradient pulses; and
a processing system configured for analyzing the signal, and communicating a report regarding said analysis.

18. The system according to claim 17, wherein each pair of bipolar gradient pulse subsequences is characterized by a different gradient direction.

19. The system according to claim 17, wherein said plurality of pairs is two pairs.

20. The system according to claim 19, wherein said radiofrequency system is configured for performing a series of experiments, each experiment being characterized by a different angle ω between the respective gradient directions of said bipolar gradient pulse subsequences, and said processing system is configured for analyzing signal profiles as a function of said angle so as to extract at least one of: shape information and size information from the sample.

21. The system of claim 20, wherein said processing system is configured for generating an estimate of eccentricity distribution of restricted compartments in the sample, to provide said shape information.

22. The system according to claim 17, wherein said processing system is configured for analyzing said signal as a function of a magnetic resonance wavenumber so as to generate an estimate of a size distribution of restricted compartments.

23. The system according to claim 17, wherein said processing system is configured for generating a magnetic resonance image of the sample based on the signal.

24. A computer software product, comprising a computer-readable medium in which program instructions are stored, which instructions, when read by a computer, cause the computer to instruct a radiofrequency system to generate a plurality of pairs of bipolar gradient pulse subsequences,
wherein each bipolar gradient pulse subsequence of each pair comprises:
a first gradient pulse corresponding to a first activation of a gradient coil at a first amplitude for a first period of time,
a second gradient pulse corresponding to a second activation of said gradient coil at a second amplitude for a second period of time, and
a radiofrequency sequence in which both said first gradient pulse and said second gradient pulse are embedded,
wherein said first and said second activations are along a gradient direction specific to said pair,
wherein said first and second amplitudes are of opposite polarity, and wherein, in each pair, there is at least one radiofrequency pulse between every two successive gradient pulses.

25. A computer software product, comprising a computer-readable medium in which program instructions are stored, which instructions, when read by a computer, cause the computer to receive a recorded magnetic resonance signal in response to a plurality of pairs of bipolar gradient pulse subsequences, to analyze said signal, and to communicate a report regarding said analysis, wherein each bipolar gradient pulse subsequence of each pair comprises:
a first gradient pulse corresponding to a first activation of a gradient coil at a first amplitude for a first period of time,
a second gradient pulse corresponding to a second activation of said gradient coil at a second amplitude for a second period of time, and
a radiofrequency sequence in which both said first gradient pulse and said second gradient pulse are embedded,
wherein said first and said second activations are along a gradient direction specific to said pair,
wherein said first and second amplitudes are of opposite polarity, and
wherein, in each pair, there is at least one radiofrequency pulse between every two successive gradient pulses.

* * * * *